US006495525B1

(12) United States Patent
Lee et al.

(10) Patent No.: US 6,495,525 B1
(45) Date of Patent: Dec. 17, 2002

(54) VLA-4 INHIBITOR: OMEPUPA-V

(75) Inventors: Wen-Cherng Lee, Lexington; Alan Gill, Reading, both of MA (US)

(73) Assignee: Biogen, Inc., Cambridge, MA (US)

( * ) Notice: Subject to any disclaimer, the term of this patent is extended or adjusted under 35 U.S.C. 154(b) by 0 days.

(21) Appl. No.: 09/724,107

(22) Filed: Nov. 28, 2000

Related U.S. Application Data

(63) Continuation of application No. PCT/US99/11924, filed on May 28, 1999.
(60) Provisional application No. 60/087,064, filed on May 28, 1998.

(51) Int. Cl.$^7$ ..................... A61K 31/401; C07D 207/14

(52) U.S. Cl. ......................................... 514/43; 548/537

(58) Field of Search ........................... 548/537; 514/423

(56) References Cited

U.S. PATENT DOCUMENTS

| | | | |
|---|---|---|---|
| 4,725,583 A | 2/1988 | Luly et al. | 514/18 |
| 4,826,815 A | 5/1989 | Luly et al. | 514/19 |
| 5,260,277 A | 11/1993 | McKenzie | 544/18 |
| 5,314,902 A | 5/1994 | Tjoeng et al. | 514/357 |
| 5,434,188 A | 7/1995 | Boschelli et al. | 514/617 |
| 5,770,573 A | 6/1998 | Arrhenius et al. | 514/18 |

FOREIGN PATENT DOCUMENTS

| | | |
|---|---|---|
| DE | 43 09 867 | 9/1994 |
| EP | 0 565 896 | 10/1903 |
| EP | 0 021 234 | 1/1981 |
| EP | 0 460 679 | 12/1991 |
| EP | 0 519 748 | 12/1992 |
| WO | WO 89/09786 | 10/1989 |
| WO | WO 91/09837 | 7/1991 |
| WO | WO 92 00995 | 1/1992 |
| WO | WO 92 08464 | 5/1992 |
| WO | WO 93 08823 | 5/1993 |
| WO | WO 93 09795 | 5/1993 |
| WO | WO 93 12809 | 7/1993 |
| WO | WO 94 02445 | 2/1994 |
| WO | WO 94 15958 | 5/1994 |
| WO | WO 94 23714 | 10/1994 |
| WO | WO 95 15973 | 12/1994 |
| WO | WO 96 22966 | 8/1996 |
| WO | WO 97 03094 | 1/1997 |
| WO | WO 98/04913 | 2/1998 |

OTHER PUBLICATIONS

Thierry et al., "Synthesis and Activity of NAcSerAspLysPro Analogues on Cellular Interactions between T–Cell and Erythrocytes in Rosette Formation," Journal of Medical Chemistry, 1990, 33: 2122–2127.

Greenstein et al., "Chemistry of the Amino Acids," John Wiley and Sons, Inc., vol. 2, 1162–1186.

Kim et al., "Inhibition of $^{125}$I–Labeled Ristocetin Binding to Micrococcus Lutcus Cells by the Peptides Related to Bacterial Cell Wall Mucopeptide Precursors: Quantitative Structure–Activity Relationships," Journal Medical Chemistry, 1989, 32: 84–93.

Abraham et al., $\alpha_4$–Integrins Mediate Antigen–induced Late Bronchial Responses and Prolonged Airway hyperresposiveness in sheep, J Clin. Invest. 1994, 93(2):776–787.

Bajusz et al., "Design and Synthesis of Peptide Inhibitors of Blood Coagulation", Folia Haematol. Leipzig, 1982, 109:16–21.

Baldwin et al., Chemical Abstracts 1988, 108: 127408t.

Chen et al., Chemical Abstracts 1991, 115: 159756r.

Chisholm et al., "Monoclonal antibodies to the integrin α–4 subunit inhibit the murine contact hypersensitivity response", European Journal of Immunology, 1993, 23:682–688.

Elices et al., "Expression and Functional Significance of Alternatively Spliced CS1 Fibronectin in Rheumatoid Arthritis Microvasculature", The Journal of Clinical Investigation, 1994, 93:405–416.

Ferguson et al., "Two integrin–binding peptides abrogate T cell–mediated immune responses in vivo", Proceedings of the National Academy of Sciences USA, 1991, 88:8072–8076.

Ferguson et al., "Antigen–Independent Processes in Antigen–Specific Immunity", The Journal of Immunology, 1993, 150:1172–1182.

Goodman et al., "Synthesis and Conformation of Sequential Polypeptides of L–alanine and beta–Aminobutyric Acid", Macromolecules, 1976, 9:1–6.

Gruszecki et al., "Diacylamine–perfekte Acylierungsmittel für die Peptidsynthese", Liebigs Ann. Chem., 1988, 331–336.

Hemler, "VLA Proteins in the Integrin Family: Structures, Functions, and Their Role on Leukocytes", Annual Review of Immunology, 1990, 8:365–400.

Jiang et al., "Approaches Toward the Total Synthesis of Astins A, B, And C", Tetrahedron Letters, 1994, 35:2121–4.

Komoriya et al., "The Minimal Essential Sequence for a Major Cell Type–specific Adhesion site (CSI) within the Alternatively Spliced . . . ", Journal of Biological Chemistry, 1991, 266:15075–15079.

Lampi et al., Chemical Abstracts 1993, 118: 73614t.

Lobb et al., "The Pathophysiologic Role of α4 Integrins in Vivo", The Journal of Clinical Investigation, 1994, 94:1722–1728.

(List continued on next page.)

*Primary Examiner*—Robert Gerstl
(74) *Attorney, Agent, or Firm*—Fish & Richardson P.C.

(57) ABSTRACT

OMePUPA-V, (R)-N-[[4-[[(2-methylphenylamino) carbonyl]amino]phenyl]acetyl]-L-prolyl-3-methyl)-β-Alanine, a cell adhesion inhibitor, pharmaceutical compositions, and methods of treatment of cell-adhesion mediated pathologies.

19 Claims, 5 Drawing Sheets

OTHER PUBLICATIONS

Molossi et al., "Blockade of Very Late Antigen–4 Integrin Binding to Fibronectin with Connecting Segment–1 Peptide Reduces Accelerated Coronary Arteriopathy . . . ", Journal of Clinical Investigation, 1995, 95:2601–2610.

Morales–Ducret et al., "$\alpha_4\beta_1$ Integrin (VLA–4) Ligands in Arthritis Vascular Cell Adhesion Molecule–1 Expression in Synovium and on . . . ", The Journal of Immunology, 1992, 149:1424–1431.

Narumiya et al., "Pre–B cells adhere to fibronectin via interactions of integrin $\alpha 5/\alpha v$ with RGDS as well as of integrin $\alpha 4$ with two distinct V region sequences at its different . . . ", Intl. Immun., 1994, 6:139–147.

Nowlin et al.; "A Novel Cyclic Pentapeptide Inhibits $\alpha 4\beta 1$ and $\alpha 5\beta 1$ Integrin–mediated Cell Adhesion", The Journal of Biological Chemistry, 1993, 268:20352–20359.

Subasinghe et al., "Synthesis of Acyclic and Dehydroaspartic Acid Analogues of Ac–Asp–Glu–OH and Their Inhibition of Rat Brain N–Acetylated alpha–Linked Acidic Dipeptidase (NAALA Dipeptidase)", Journal of Medicinal Chemistry, 1990, 33:2734–44.

Wayner et al., "Activation–dependent Recognition by Hematopoietic Cells of the LDV Sequence in the V Region of Fibronectin", The Journal of Cell Biology, 1992, 116:489–497.

Yednock et al., "Prevention of experimental automimmune encephalomyelitis by antibodies against $\alpha 4\beta 1$ integrin", Nature, 1992, 356:63–66.

Goodman et al, The pharmacological basis of therapeutics. $6^{th}$ ed, New York, Macmillan Publishing Inc., 1980, 1738–1740.

VLA-4 INHIBITOR: OMEPUPA-V

This is a continuation of PCT application Ser. No. PCT/US99/11924, filed May 28, 1999, which claims priority from U.S. Provisional application 60/087,064 filed May 28,1998.

The present invention relates to novel compounds that are useful for inhibition, alteration, or prevention of cell adhesion and cell adhesion-mediated pathologies. This invention also relates to pharmaceutical formulations comprising these compounds, and methods of using them for inhibition and prevention of cell adhesion and cell adhesion-mediated pathologies. The compounds and pharmaceutical compositions of this invention can be used as therapeutic or prophylactic agents. They are particularly well suited for the treatment of many inflammatory and autoimmune diseases.

BACKGROUND OF THE INVENTION

Cell adhesion is a process by which cells associate with each other, migrate towards a specific target or localize within the extra-cellular matrix. As such, cell adhesion constitutes one of the fundamental mechanisms underlying numerous biological phenomena. For example, cell adhesion is responsible for the adhesion of hematopoietic cells to endothelial cells and the subsequent migration of those hematopoietic cells out of blood vessels and to the site of injury. As such, cell adhesion plays a role in numerous pathologies such as, for example, inflammation and immune reactions in mammals.

Investigations into the molecular basis for cell adhesion have revealed that various cell-surface macromolecules—collectively known as cell adhesion molecules or receptors—mediate cell-cell and cell-matrix interactions. For example, proteins of the superfamily called "integrins" are key mediators in adhesive interactions between hematopoietic cells and their microenvironment (M. E. Hemler, "VLA Proteins in the Integrin Family: Structures, Functions, and Their Role on Leukocytes." *Ann. Rev. Immunol.*, 8, p. 365 (1990)). Integrins are non-covalent heterodimeric complexes consisting of two subunits called $\alpha$ and $\beta$. There are at least 17 different $\alpha$ subunits ($\alpha1$–$\alpha10$, $\alpha$-L, $\alpha$-M, $\alpha$-D, $\alpha$-X, $\alpha$-IIB, $\alpha$-V and $\alpha$-E) and at least 9 different $\beta$($\beta1$–$\beta9$) subunits which have been identified to date. Based on the type of its $\alpha$ and $\beta$ subunit components, each integrin molecule can be categorized into a subfamily.

Integrin $\alpha4\beta1$, also known as very late antigen-4 ("VLA-4") or CD49d/CD29, is a leukocyte cell surface receptor that participates in a wide variety of both cell-cell and cell-matrix adhesive interactions (M. E. Hemler, *Ann. Rev. Immunol.*, 8, p. 365 (1990)). It serves as a receptor for the cytokine-inducible endothelial cell surface protein, vascular cell adhesion molecule-1 ("VCAM-1"), as well as for the extracellular matrix protein fibronectin ("FN") (Ruegg et al., *J. Cell Biol.*, 177, p. 179 (1991); Wayner et al., *J. Cell Biol.*, 105, p. 1873 (1987); Kramer et al., *J. Biol. Chem.*, 264, p. 4684 (1989); Gehlsen et al. *Science*, 24, p. 1228 (1988)). Anti-VLA-4 monoclonal antibodies ("mAb's") have been shown to inhibit VLA-4-dependent adhesive interactions both in vitro and in vivo (Ferguson et al. *Proc. Natl. Acad. Sci.*, 88, p. 8072 (1991); Ferguson et al., *J. Immunol.*, 150, p. 1172 (1993)). Results of in vivo experiments suggest that the inhibition of VLA-4-dependent cell adhesion may prevent, inhibit or alter several inflammatory and autoimmune pathologies. (R. L. Lobb et al., "The Pathophysiologic Role of $\alpha4$ Integrins In Vivo", *J. Clin. Invest.*, 94, pp. 1722–28 (1994)).

In order to identify the minimum active amino acid sequence necessary to bind VLA-4, Komoriya et al. synthesized a variety of overlapping peptides based on the amino acid sequence of the CS-1 region (the VLA-4 binding domain) of a particular species of fibronectin. ("The Minimal Essential Sequence for a Major Cell Type-Specific Adhesion Site (CS1) Within the Alternatively Spliced Type III Connecting Segment Domain of Fibronectin Is Leucine-Aspartic Acid-Valine", *J. Biol. Chem.*, 266 (23), pp. 15075–79 (1991)). They identified an 8-amino acid peptide, Glu-Ile-Leu-Asp-Val-Pro-Ser-Thr, as well as two smaller overlapping pentapeptides, Glu-Ile-Leu-Asp-Val and Leu-Asp-Val-Pro-Ser, that possessed inhibitory activity against FN-dependent cell adhesion. These results suggested that the tripeptide Leu-Asp-Val was the minimum sequence for cell-adhesion activity. It was later shown that Leu-Asp-Val binds only to lymphocytes that express an activated form of VLA-4, thus casting doubt on the utility of such a peptide in vivo (E. A. Wayner et al., "Activation-Dependent Recognition by Hematopoietic Cells of the LDV Sequence in the V Region of Fibronectin", *J. Cell. Biol.*, 116(2), pp. 489–497 (1992)). However, certain larger peptides containing the LDV sequence were subsequently shown to be active in vivo (T. A. Ferguson et al., "Two Integrin Binding Peptides Abrogate T-cell-Mediated Immune Responses In Vivo", *Proc. Natl. Acad. Sci. USA*, 88, pp. 8072–76 (1991); and S. M. Wahl et al., "Synthetic Fibronectin Peptides Suppress Arthritis in Rats by Interrupting Leukocyte Adhesion and Recruitment", *J. Clin. Invest.*, 94, pp. 655–62 (1994)). A cyclic pentapeptide which can inhibit both VLA-4 and VLA-5 adhesion to FN has also been described. (See, e.g., D. M. Nowlin et al. "A Novel Cyclic Pentapeptide Inhibits $\alpha4\beta1$ and $\alpha5\beta1$ Integrin-mediated Cell Adhesion", *J. Biol. Chem.*, 268(27), pp. 20352–59 (1993); and PCT publication PCT/US91/04862). This pentapeptide was based on the tripeptide sequence Arg-Gly-Asp from FN which had been known as a common motif in the recognition site for several extracellular-matrix proteins.

Examples of other VLA-4 inhibitors have been reported, for example, in copending United States patent application 08/376,372, specifically incorporated by reference herein. U.S. Ser. No. 376,372 describes linear peptidyl compounds containing $\beta$-amino acids which have cell adhesion inhibitory activity. International patent applications WO 94/15958 and WO 92/00995, specifically incorporated by reference, describe cyclic peptide and peptidomimetic compounds with cell adhesion modulating activity. International patent applications WO 93/08823 and WO 92/08464 (specifically incorporated by reference herein) describe guanidinyl-, urea- and thiourea-containing cell adhesion modulating compounds. U.S. Pat. No. 5,260,277 describes guanidinyl cell adhesion modulation compounds, and is also specifically incorporated herein.

Despite these advances, there remains a need for low molecular weight, specific inhibitors of VLA-4 dependent cell adhesion that have improved pharmacokinetic and pharmacodynamic properties such as oral bioavailability and significant duration of action. Such compounds would provide useful agents for treatment, alteration, prevention or suppression of various pathologies mediated by cell adhesion and VLA-4 binding.

SUMMARY OF THE INVENTION

The compounds of the present invention are inhibitors of the VLA-4 integrin, thereby blocking the binding of VLA-4 to its various ligands, such as VCAM-1 and regions of fibronectin. Thus these compounds are useful in inhibiting cell adhesion processes including cell activation, migration, proliferation and differentiation. These compounds are useful for inhibition, prevention and suppression of VLA-4-mediated cell adhesion and pathologies associated with that adhesion, such as inflammation and immune reactions, including for example, multiple sclerosis, asthma, allergic rhinitis, allergic conjunctivitis, inflammatory lung diseases, rheumatoid arthritis, septic arthritis, type 1 diabetes, organ transplantation, restenosis, autologous bone marrow transplantation, inflammatory sequelae of viral infections, myocarditis, inflammatory bowel disease including ulcerative colitis and Crohn's disease, certain types of toxic and immune-based nephritis, contact dermal hypersensitivity, psoriasis, tumor metastasis, multiple myeloma, and atherosclerosis. The compounds of this invention may be used alone or in combination with other therapeutic or prophylactic agents to inhibit, alter, prevent or suppress cell adhesion. This invention also provides pharmaceutical formulations containing these VLA-4-mediated cell adhesion inhibitors and methods of using the compounds and compositions of the invention for inhibition of cell adhesion.

DETAILED DESCRIPTION

Figure 1:
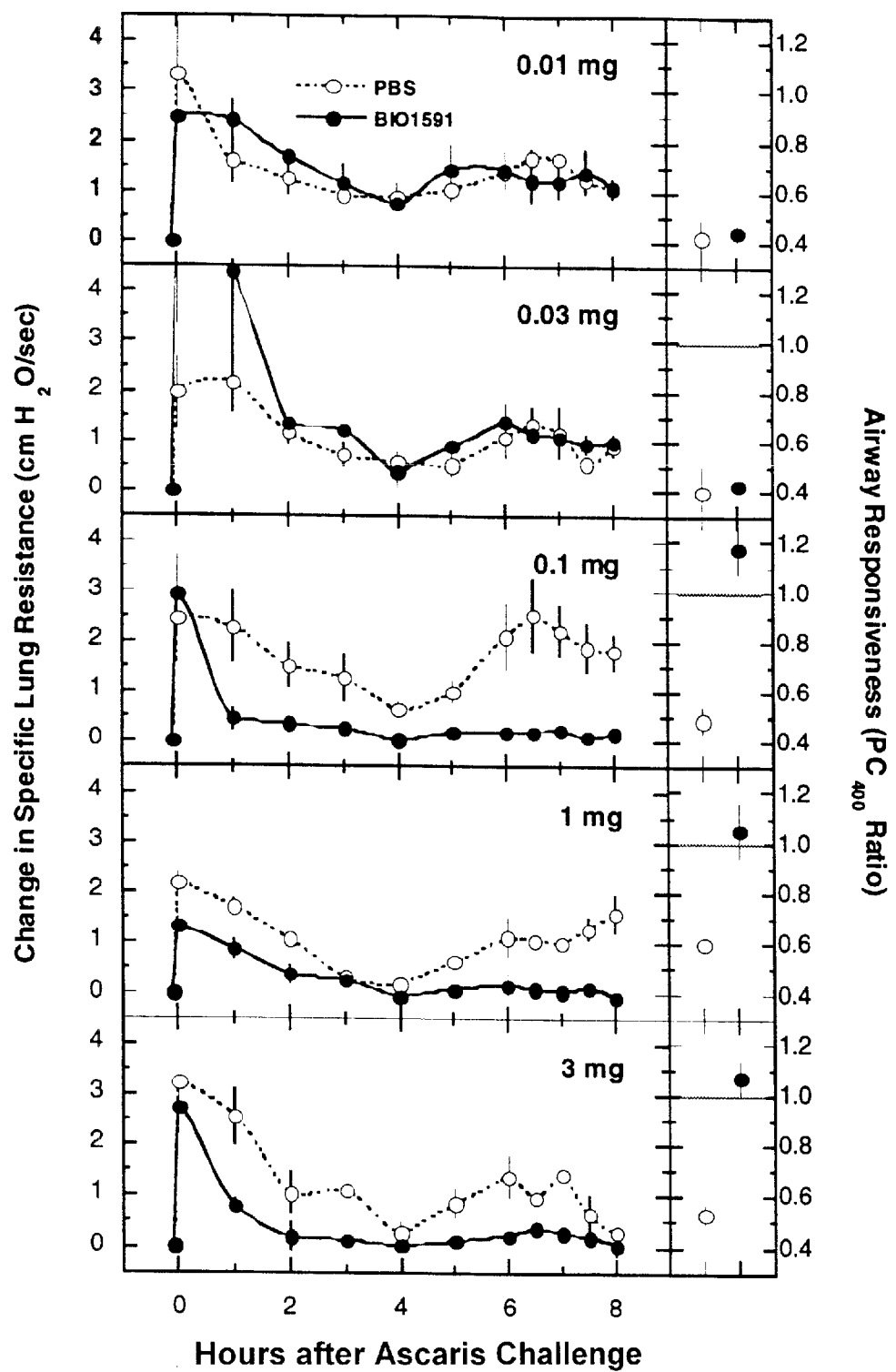
FIG. 1 reports the airway responsiveness of sheep after treatment with oMePUPA-V. Sheep, naturally sensitive to *Ascaris suum*, were challenged with an aerosol of *Ascaris suum* allergen 2 h after aerosol administration of oMePUPA-V at the indicated doses or an equivalent amount of vehicle. Pulmonary mechanics were measured at the indicated times and are reported as the change in specific airways resistance from the pre-study baseline value (left panels). Airways resistance to inhaled carbachol was determined prior to study initiation and at 24 h post-allergen challenge (right panels). Airways responsiveness is reported as the $PC_{400}$ (amount of carbachol required to increase resistance by 400%) ratio by comparison of pre-challenge and post-challenge values

The present invention provides compounds which are capable of inhibiting VLA-4 mediated cell adhesion by inhibiting the binding of ligands to that receptor. The preferred compound is (R)-N-[[4-[[(2-methylphenylamino)carbonyl]amino]phenyl]acetyl]-L-prolyl-3-methyl)-β-Alanine, referred to herein as "oMePUPA-V", represented by the following formula I:

BIO 1591 and is referred to herein as "oMePUPA-V". The invention is also intended to encompass pharmaceutically acceptable derivatives, salts, and esters of oMePUPA-V.

Compounds of Formula I contain one or more asymmetric centers and thus can occur as racemic mixtures, single enantiomers, diastereomeric mixtures and individual diastereomers. The present invention is meant to comprehend all such isomeric forms of the compound of Formula I.

The claimed invention is also intended to encompass pharmaceutically acceptable salts of Formula I. The term "pharmaceutically acceptable salts" refers to salts prepared from pharmaceutically acceptable non-toxic bases or acids including inorganic or organic bases and inorganic or organic acids. Salts derived from inorganic bases include aluminum, ammonium, calcium, copper, ferric, ferrous, lithium, magnesium, manganic salts, manganous, potassium, sodium, zinc, and the like. Particularly preferred are the ammonium, calcium, magnesium, potassium and sodium salts.

Salts derived from pharmaceutically acceptable organic non-toxic bases include salts of primary, secondary, and tertiary amines, substituted amines including naturally occurring substituted amines, cyclic amines, and basic ion exchange resins, such as arginine, betaine, caffeine, choline, N,N'-dibenzylethylenediamine, diethylamine, 2-diethylaminoethanol, 2-dimethylaminoethanol, ethanolamine, ethylenediamine, N-ethyl-morpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine, and the like.

When the compound of the present invention is basic, salts may be prepared from pharmaceutically acceptable non-toxic acids, including inorganic and organic acids. Such acids include acetic, benzenesulfonic, benzoic, camphorsulfonic, citric, ethanesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid, and the like. Particularly preferred are citric, hydrobromic, hydrochloric, maleic, phosphoric, sulfurric and tartaric acids.

Additionally, the claimed invention encompasses prodrugs, specifically, ester prodrugs wherein the carboxyl group of:

(R)-N-[[4-[[(2-methylphenylamino)carbonyl]amino] phenyl]acetyl]-L-prolyl-3-methyl)-β-Alanine is esterified with any of the alcohols. Preferred alcohols are methanol, ethanol, propanol, butanol, or straight or branched chain alkyl C1-10 alcohols.

The ability of the compounds of Formula I to antagonize the actions of VLA-4 makes them useful for preventing, treating, or reversing the symptoms, disorders or diseases induced by the binding of VLA-4 to its ligands. Thus these antagonists will inhibit cell adhesion processes including cell activation, migration, proliferation and differentiation. Accordingly, another aspect of the present invention provides methods for the treatment, prevention, alleviation, or suppression of diseases or disorders mediated by the VLA-4 pathway. Such diseases and disorders include, for example, asthma, multiple sclerosis, allergic rhinitis, allergic conjunctivitis, inflammatory lung diseases, rheumatoid arthritis, multiple myeloma, septic arthritis, type I diabetes, organ transplant rejection, inflammatory bowel disease, and others.

Compounds of this invention may be synthesized using any conventional technique, several of which are exemplified herein. Preferably, these compounds are chemically synthesized from readily available starting materials, such as α-amino acids and their functional equivalents. Modular and convergent methods for the synthesis of these compounds are also preferred. In a convergent approach, for example, large sections of the final product are brought together in the last stages of the synthesis, rather than by incremental addition of small pieces to a growing molecular chain.

The compounds of this invention may also be modified by appending appropriate functionalities to enhance selective biological properties. Such modifications are known in the art and include those which increase biological penetration into a given biological system (e.g., blood, lymphatic system, central nervous system), increase oral availability, increase solubility to allow administration by injection, alter metabolism and alter rate of excretion. Examples of these modifications include, but are not limited to, esterification with polyethylene glycols, derivatization with pivolates or fatty acid substituents, conversion to carbamates, hydroxylation of aromatic rings, and heteroatom-substitution in aromatic rings.

As used throughout this application, the term "patient" refers to mammals, including humans. And the term "cell" refers to any cell, preferably mammalian cells, including human cells.

Once synthesized, the activities and VLA-4 specificities of the compounds according to this invention may be determined using in vitro and in vivo assays.

For example, the cell adhesion inhibitory activity of these compounds may be measured by determining the concentration of inhibitor required to block the binding of VLA-4-expressing cells to fibronectin- or CS1-coated plates. In this type of assay, microtiter wells are coated with either fibronectin (containing the CS-1 sequence) or CS-1. If CS-1 is used, it must be conjugated to a carrier protein, such as bovine serum albumin, in order to bind to the wells. Once the wells are coated, varying concentrations of the test compound are then added together with appropriately labeled VLA-4-expressing cells. Alternatively, the test compound may be added first and allowed to incubate with the coated wells prior to the addition of the cells. The cells are allowed to incubate in the wells for at least 30 minutes. Following incubation, the wells are emptied and washed. Inhibition of binding is measured by quantitating the fluorescence or radioactivity bound to the plate for each of the various concentrations of test compound, as well as for controls containing no test compound.

VLA-4-expressing cells that may be utilized in this assay include Ramos cells, Jurkat cells, A375 melanoma cells, as well as human peripheral blood lymophocytes (PBLs). The cells used in this assay may be labeled in any appropriate manner, for example fluorescently or radioactively labeled.

A direct binding assay may also be employed to quantitate the inhibitory activity of the compounds of this invention. In this assay, a VCAM-IgG fusion protein containing the first two immunoglobulin domains of VCAM (D1D2) attached above the hinge region of an IgG1 molecule ("VCAM 2D-IgG"), is conjugated to a marker enzyme, such as alkaline phosphatase ("AP"). The synthesis of this VCAM-IgG fusion is described in PCT publication WO 90/13300, the disclosure of which is herein incorporated by reference. The conjugation of that fusion to a marker enzyme is achieved by cross-linking methods well-known in the art.

The VCAM-IgG enzyme conjugate is then placed in the wells of a multi-well filtration plate, such as that contained in the Millipore Multiscreen Assay System (Millipore Corp., Bedford, Ma.). Varying concentrations of the test inhibitory compound are then added to the wells followed by addition of VLA-4-expressing cells. The cells, compound and VCAM-IgG enzyme conjugate are mixed together and allowed to incubate at room temperature.

Following incubation, the wells are vacuum drained, leaving behind the cells and any bound VCAM. Quantitation of bound VCAM is determined by adding an appropriate colorimetric substrate for the enzyme conjugated to VCAM-IgG and determining the amount of reaction product. Decreased reaction product indicates increased binding inhibitory activity. The protocol for certain assays is described below:

In order to assess the VLA-4 inhibitory specificity of the compounds of this invention, assays for other major groups of integrins, i.e., β2 and β3, as well as other β1 integrins, such as VLA-5, VLA-6 and α4β7 are performed. These assays may be similar to the adhesion inhibition and direct binding assays described above, substituting the appropriate integrin-expressing cell and corresponding ligand. For example, polymorphonuclear cells (PMNs) express β2 integrins on their surface and bind to ICAM. β3 integrins are involved in platelet aggregation and inhibition may be measured in a standard platelet aggregation assay. VLA-5 binds specifically to Arg-Gly-Asp sequences, while VLA-6 binds to laminin. α4β7 is a recently discovered homologue of VLA-4, which also binds fibronectin and VCAM. Specificity with respect to α4β7 is determined in a binding assay that utilizes the above-described VCAM-IgG-enzyme marker conjugate and a cell line that expresses α4β7, but not VLA-4, such as RPMI-8866 or JY cells.

Once VLA-4-specific inhibitors are identified, they may be further characterized in in vivo assays. One such assay tests the inhibition of contact hypersensitivity in an animal, such as described by P. L. Chisholm et al., "Monoclonal Antibodies to the Integrin α-4 Subunit Inhibit the Murine Contact Hypersensitivity Response", *Eur. J. Immunol.*, 23, pp. 682–688 (1993) and in "Current Protocols in Immunology", J. E. Coligan, et al., Eds., John Wiley & Sons, New York, 1, pp. 4.2.1–4.2.5 (1991), the disclosures of which are herein incorporated by reference. In this assay, the skin of the animal is sensitized by exposure to an irritant, such as dinitrofluorobenzene, followed by light physical irritation, such as scratching the skin lightly with a sharp edge. Following a recovery period, the animals are re-sensitized following the same procedure. Several days after sensitization, one ear of the animal is exposed to the chemical irritant, while the other ear is treated with a non-irritant control solution. Shortly after treating the ears, the animals are given various doses of the VLA-4 inhibitor by subcutaneous injection. In vivo inhibition of cell adhesion-associated inflammation is assessed by measuring the ear swelling response of the animal in the treated versus untreated ear. Swelling is measured using calipers or other suitable instrument to measure ear thickness. In this manner, one may identify those inhibitors of this invention which are best suited for inhibiting inflammation.

Another in vivo assay that may be employed to test the inhibitors of this invention is the sheep asthma assay. This assay is performed essentially as described in W. M. Abraham et al., "α4-Integrins Mediate Antigen-induced Late Bronchial Responses and Prolonged Airway Hyperresponsiveness in Sheep", *J. Clin. Invest.*, 93, pp. 776–87 (1994), the disclosure of which is herein incorporated by reference. This assay measures inhibition of Ascaris antigen-induced late phase airway responses and airway hyperresponsiveness in allergic sheep. The compounds of this invention may also be tested in a platelet aggregation assay.

The VLA-4 inhibitors of the invention have shown surprisingly favorable activity and selectivity. Generally, these compounds are selective for VLA-4 (>1000-fold versus α4β7 and α5β1), negative in routine PanLabs and non-GLP Ames Assays, clean in standard ancillary pharmacology tests and effective in the sheep model following once-a-day dosing at predicted use level in man of 1 mg/day or less.

The claimed compounds have surprisingly superior potency as compare to structurally related VLA-4 inhibitors. For example, in Ascaris-sensitive sheep treated once daily for four days with nebulized drug at 0.1 mg/kg and then challenged with antigen 24 hours after the last dose, previously tested compounds substantially attenuated the early response and blocked late phase bronchoconstriction and the development of non-specific hyperresponsiveness. Assuming bioequivalence in man, a total dose of 7 mg would be required in a 70 kg person. Furthermore, drug was administered to the sheep through an endotracheal tube at deposition rates estimated to be 2-fold greater than is typically achieved in man with oral inhaler devices. Additionally, it is likely that excipients will need to be added to the final solid formulation to optimize device filling and drug delivery. These factors suggest a possible dose requirement in man of 14 mg or more which exceeds the technical limit of 1–5 mg, that can be delivered in one actuation through a dry powder inhaler (DPI) device. While the necessary dose could be delivered by multiple actuations of the DPI, this would represent a competitive disadvantage in the asthma market where typical inhaled steroid doses are 0.2–1.0 mg.

oMePUPA-V attenuated the early response, blocked late-phase bronchoconstriction and normalized hyperresponsiveness at a minimum dose of 0.003 mg/kg when administered as a single nebulized dose 2 hours before antigen challenge. Moreover, a daily dose of 0.001 mg/kg for 4 days with antigen challenge 24 hours after the last dose gives a maximum response. Thus, oMePUPA-V is 30 to 100-fold more potent than previous compounds, with dose levels in the range of the best marketed inhaled steroids. oMePUPA-V, as well as the penultimate synthetic intermediate, is highly crystalline. (See FIG. 1, Table 1)

Additionally, oMePUPA-V has an improved metabolic profile as compared to known VLA-4 inhibitor compounds. For example, following aerosol administration, the claimed compounds were rapidly converted to a less active metabolite, which was the predominant product recovered from bronchoalveolar lavage fluid (BALF) and was also the predominant product observed in the systemic circulation where it exhibited a longer plasma half-life than the parent compound. While rapid metabolic conversion to less active compounds is a useful strategy to achieve reduced systemic exposure, compounds which are metabolized to by-products with little or no intrinsic activity present fewer complexities in development and are preferred from a backup perspective.

The potential proteolytic products of oMePUPA-V are inactive in VLA-4 binding assays so proteolysis would generate inactive products regardless. Nevertheless, in vitro metabolism studies as well as in vivo PK studies in rat, dog and sheep have shown oMePUPA-V to be proteolytically stable.

TABLE 1

Properties of oMePUPA-V compared to previously known inhibitors.

| Property | Previous Cmpd | oMePUPA-V |
|---|---|---|
| $IC_{50}$ against VLA-4-VCAM-Ig binding | 1.5 nM | 2.7 nM |
| $IC_{50}$ against α4β7-VCAM-Ig binding | 2.7 μM | >100 μM |
| $IC_{50}$ against α5β1-FN adhesion | >100 μM | >100 μM |
| Minimum effective dose in sheep model | | |
| single dose | 0.1 mg/kg | 0.003 mg/kg |
| repeat-dose | 0.03–0.1 mg/kg | 0.001 mg/kg |
| Crystallinity | NO | YES |
| In vitro pharma screen 85 tests | 1 weak hit | clean |
| ACE activity | ACE substrate | clean |
| Glucuronidation | low levels | planned |
| Ames test (mutagenicity) | clean | clean |
| Ancillary pharmacology (side-effects) | clean | |
| Systemic exposure, 10 mg aerosol dose (sheep) | 40 ng/ml × hr | finished |
| Metabolic profile | active metabolite | |
| Oral availability | <1% | <1% |
| Bulk stability (40° C., 75% RH) | "unstable" | stable >4 wk |
| Formulated stability (40° C.) | 0.2% degradation/day | stable >4 wk |

The compounds of the present invention may be formulated into pharmaceutical compositions that may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrastemal, intrathecal, intrahepatic, intralesional and intracranial injection or infusion techniques.

The pharmaceutical compositions of this invention comprise any of the compounds of the present invention, or pharmaceutically acceptable derivatives thereof, together with any pharmaceutically acceptable carrier. The term "carrier" as used herein includes acceptable adjuvants and vehicles. Pharmaceutically acceptable carriers that may be used in the pharmaceutical compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protarnine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

According to this invention, the pharmaceutical compositions may be in the form of a sterile injectable preparation, for example a sterile injectable aqueous or oleaginous suspension. This suspension may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed including synthetic mono- or di-glycerides. Fatty acids, such as oleic acid and its glyceride derivatives are useful in the preparation of injectables, as do natural pharmaceutically-acceptable oils, such as olive oil or castor oil, especially in their polyoxyethylated versions. These oil solutions or suspensions may also contain a long-chain alcohol diluent or dispersant.

The pharmaceutical compositions of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at the rectal temperature and therefore will melt in the rectum to release the drug. Such materials include cocoa butter, beeswax and polyethylene glycols.

The pharmaceutical compositions of this invention may also be administered topically, especially when the target of treatment includes areas or organs readily accessible by topical application, including, for example, diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with our without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation through the use of a nebulizer, a dry powder inhaler or a metered dose inhaler. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents. Additionally, the compositions of the invention may include any pharmaceutically acceptable carriers, such as, for example, lactose for dry powder formulations.

The amount of active ingredient that may be combined with the carrier materials to produce a single dosage form will vary depending upon the host treated, and the particular mode of administration. It should be understood, however, that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of active ingredient may also depend upon the therapeutic or prophylactic agent, if any, with which the ingredient is co-administered.

The dosage and dose rate of the compounds of this invention effective to prevent, suppress or inhibit cell adhesion will depend on a variety of factors, such as the nature of the inhibitor, the size of the patient, the goal of the treatment, the nature of the pathology to be treated, the specific pharmaceutical composition used, and the judgment of the treating physician. Dosage levels of between about 0.001 and about 100 mg/kg body weight per day, preferably between about 0.01 to about 50 mg/kg and more preferably about 10 mg/kg body weight per day of the active ingredient compound are useful.

For use where a composition for intravenous administration is employed, a suitable dosage range is from about 0.001 mg to about 25 mg/kg, more preferably, about 0.01 mg to about 1 mg/kg.

According to another embodiment compositions containing a compound of this invention may also comprise an additional agent selected from the group consisting of corticosteroids, bronchodilators, antiasthmatics (mast cell stabilizers), antiinflammatories, antirheumatics, immunosuppressants, antimetabolites, immunonodulators, antipsoriatics and antidiabetics. Specific compounds within each of these classes may be selected from any of those listed under the appropriate group headings in "Comprehensive Medicinal Chemistry", Pergamon Press, Oxford, England, pp. 970–986 (1990), the disclosure of which is herein incorporated by reference. Also included within this group are compounds such as theophylline, sulfasalazine and aminosalicylates (antiinflammatories); cyclosporin, FK-506, and rapamycin (immunosuppressants); cyclophosphamide and methotrexate (antimetabolites); steroids (inhaled, oral or topical) and interferons (immunomodulators). Furthermore, the compounds of the invention may be administered in conjunction with additional cell adhesion inhibitors. When administering one or more additional agents in combination with the claimed VLA-4 inhibitor, the active ingredients may be formulated together, or, alternatively may be administered in combination. Administration of one or more active agents in combination with the VLA-4 inhibitors of the claimed invention may be substantially simultaneous, or sequential. Those skilled in the art can easily determine the most appropriate application depending upon the agents to be delivered, the desired results, and the patient, and condition being treated.

According to other embodiments, the invention provides methods for preventing, inhibiting or suppressing cell adhesion-associated inflammation and cell adhesion-associated immune or autoimmune responses in a patient. VLA-4-associated cell adhesion plays a central role in a variety of inflammation, immune and autoimmune diseases. Thus, inhibition of cell adhesion by the compounds of this invention may be utilized in methods of treating or preventing inflammatory, immune and autoimmune diseases. Preferably the diseases to be treated with the methods of this invention are selected from asthma, arthritis, psoriasis, transplantation rejection, multiple sclerosis, diabetes and inflammatory bowel disease.

These methods may employ the compounds of this invention in a monotherapy or in combination with an anti-inflammatory or immunosuppressive agent. Such combination therapies include administration of the agents in a single dosage form or in multiple dosage forms administered at the same time or at different times.

EXAMPLES

Example 1

Preparation of oMePUPA-V oMePUPA-V, (R)-N-[[4-[[(2-methylphenylamino)carbonyl]amino]phenyl]acetyl]-L-prolyl-3-methyl)-β-Alanine, was prepared in a convergent synthesis from commercially manufactured succinimidyl Boc-(L)-proline (Boc-Pro-OSu; Bachem) and (R)-benzyl-3-aminobutyrate hemisulfate (Celgene Corp.). Coupling of the starting materials in $CH_2Cl_2$, in the presence of $Et_3N$, followed by hydrolysis of the Boc group with 4 N HCl in dioxane afforded the HCl salt which was recrystallized from $CH_2Cl_2$/$Et_2O$. Coupling of the HCl salt with succinimidyl-2-[4-[2-(methylphenylaminocarbonyl)]amino phenyl acetate (MPUPA-OSu), prepared from the corresponding acid, MPUPA-OH (Ricerca, Inc.), provided crystalline oMePUPA-V-benzyl ester which was catalytically hydrogenated (10% Pd/C) in $THF/H_2O$ (9:1) to provide oMePUPA-V. The final product was obtained as a white solid after recrystallization from 20% aqueous acetone.

Summary of Physical Characteristics

| | |
|---|---|
| Chemical Name: | (R)-N-[[4-[[2-methylphenylamino)carbonyl]amino]phenyl] acetyl]-L-prolyl-3-methyl)-b-Alanine, |
| Empirical Formula: | $C_{25}H_{30}N_4O_5$ |
| Molecular Weight: | 466.53 |
| Appearance: | Clean white powder |
| Melting Point: | 153.6–154.4° C. |

Scheme 1
Preparation of MPUPA-OSu (2) from MPUPA-OH (1)

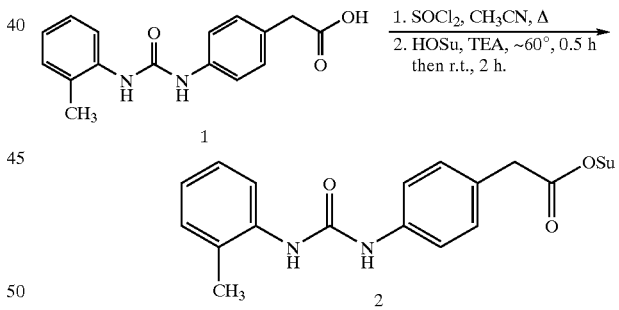

Scheme 2
Synthesis of oMePUPA-V (8) from Boc-(L)-Pro-OSu (3) and benzyl-(R)-3-aminobutyrate hemisulfate (4)

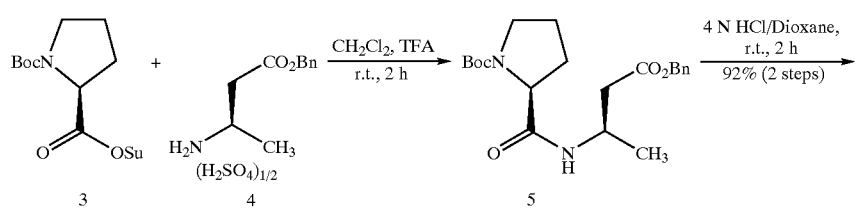

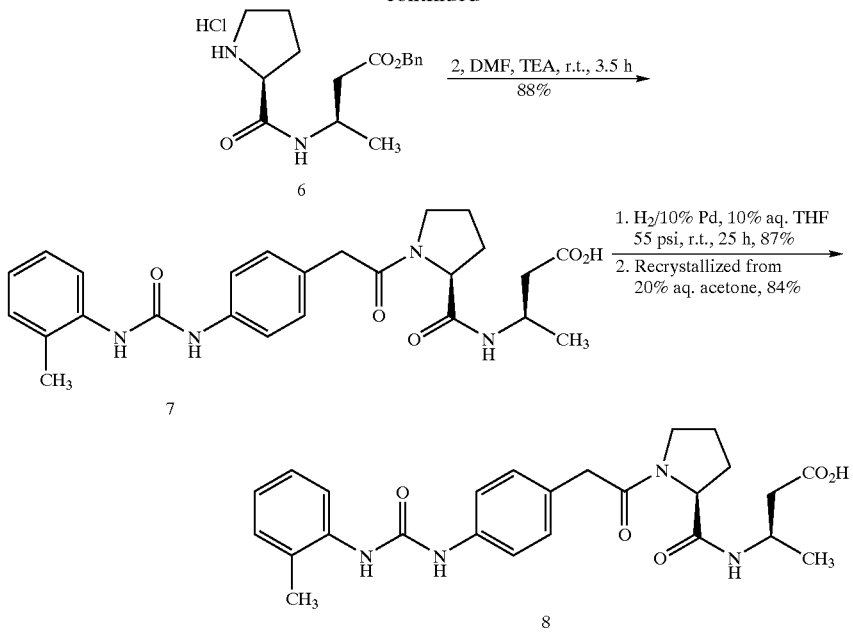

Synthesis of oMePUPA-V

The synthetic chemistry that was employed to prepare oMePUPA-V is depicted in Schemes 1 and 2. The starting materials were obtained from commercial sources and contract manufacturers: (1) was prepared in large quantity by Ricerca, Inc., Painesville, Ohio; (3) was obtained from Bachem Bioscience, Inc., King of Prussia, Pa. and (4) from Celgene Corp., Warren, N.J.

Preparation of oMePUPA-V

General analytical methods ($^1$H NMR, $^{13}$C NMR, MS, IR & HPLC)

$^1$H NMR were run either on a Bruker AC 300 or a Varian 500 or a Varian 600 instrument and samples were run either in DMSO-$d_6$ and referenced to DMSO-$d_6$ (d 2.49 ppm) or in CDCl$_3$ and referenced to residual CHCl$_3$ (d 7.24 ppm).

$^{13}$C NMR were run either on a Varian 500 or a Varian 600 instrument and samples were run either in DMSO-$d_6$ and referenced to DMSO-$d_6$ (d 40.5 ppm) or in CDCl$_3$ and referenced to CDCl$_3$ (d 77.0 ppm).

Mass Spectra were run on a Fisons VG Platform LC-MS-DS Mass Spectrometer System with a Hewlett Packard Model 1500 AutoSampler and the data processed using a Fisons VG MassLynx Mass Spectrometer Workstation. The HRMS work was run at M-Scan (PA) using Fast Atom Bombardment on a VG Analytical ZAB 2SE high field mass spectrometer with reference to SOP# MS-002, MS-006, MS-012 and MS-023. A cesium ion gun was used to generate ions for the acquired mass spectra which were recorded using a PDP-11-250J data system.

IR spectra were performed on a Perkin Elmer 1600 Series FTIR.

Analytical HPLC chromatography was performed as follows:
1. Chromatograms using Program 1 (Equilibrate @20% B, inject sample, 20% B (1 min.), 20%–70% B (24 min.), 70%–100% B (17 min.) were obtained using a Perkin Elmer Series 200 HPLC autosampler system with a Perkin Elmer 785A UV detector (set at 214 nm) and an Applied Biosystems 783A UV detector (set at 254 nm) with a PE Nelson 1020 integrator. Only the area percent values were reported.
2. Chromatograms using Program 8 (Equilibrate @15% B, inject sample, 15% B (1 min.), 15%–40% B (25 min.), 40% B (10 min.) were obtained using an Applied Biosystems 400 Solvent Delivery System with a 783A wavelength UV detector using a Waters 717 autosampler. The data was processed using a Hewlett Packard 3396 Series II integrator. The integrator was set with the following parameters: Attenuation=8, Threshold=5, Area Rejection=10000, Peak Width=0.04, Chart Speed=0.2.

All HPLC work was performed using a Vydac C-18 column (5 m pore size, 4.5 mm×25 cm, cat. #218TP54).

Solvent A (water+0.1% TFA)
Solvent B (acetonitrile+0.1% TFA)
Flow rate=1 mL/min
The gradient programs are as follows:
Program 1:Equilibrate @20% B, inject sample, 20% B (2 min.), 20%–70% B (25 min.), 100% B (5 min.).

Physical Data for [4-[[[(2-Methylphenyl)amino]carbonyl]amino]phenyl]acetic acid (1, MPUPA-OH; material manufactured by Ricerca Inc.)

mp 210–215° C. (dec.);
IR (KBr) 3295 (br band), 3034 (br band), 1707, 1637, 1603, 1551, 1516, 1457, 1414, 1302, 1241, 1189, 1118 cm$^{-1}$; $^1$H NMR (600 MHz, DMSO-$d_6$) d 12.28 (bs, 1 H), 9.0 (s, 1 H), 7.91 (s, 1 H), 7.88 (d, J=7.8 Hz, 1 H), 7.43 (d, J=8.4 Hz, 2 H), 7.19 (d, J=8.4 Hz, 2 H), 7.16 (m, 2 H), 6.94 (dd, J=7.8, 8.4 Hz, 1 H), 3.51 (s, 2 H), 2.25 (s, 3 H); $^{13}$C NMR (150 MHz, DMSO-$d_6$) d 173.0 (C), 152.7 (C), 138.5 (C), 137.5 (C), 130.2 (CH), 129.8 (CH), 128.3 (CH), 127.5 (CH), 126.2 (CH), 122.7 (CH), 121.0 (CH), 118.1 (CH), 40.1 (CH$_2$), 17.9 (CH$_3$); MS (EI) m/z 285 (M+1)$^+$, 193, 152, 134, 132, 109,108, 106, 93, 91, 57; Anal. Calcd for C$_{16}$H$_{16}$N$_2$O$_3$: C, 67.59; H, 5.67; N, 9.85; Found: C, 67.60; H, 5.70; N, 10.01.

Preparation of Succinimidyl [4[[[(2-Methylphenyl)amino]carbonyl]amino]phenyl]acetate (2, MPUPA-OSu)

To a refluxing suspension of o-methylphenylurea phenylacetic acid (1, MPUPA-OH; 150 g, 0.501 mol; from Ricerca, Inc.) in acetonitrile (600 mL) was added thionyl chloride (41 mL, 0.558 mol) over 10 min. with vigorous stirring. Large amounts of HCl evolved. The reaction mixture was cooled to room temperature with continuous stirring for 1.5 h. The reaction mixture turned into a pink slurry to which was added solid N-hydroxysuccinimide (HOSu; 75.5 g, 0.636 mol) in one portion. To this mixture triethylamine (174 mL) was added dropwise over 30 min while the temperature of the reaction mixture was maintained below 60° C. with a water bath. Stirring was continued for 2 h and then distilled water (500 mL) was added to the reaction mixture. The solid was filtered and washed with 2 L of distilled water, and acetonitrile (2×200 mL), air-dried, and further dried over $P_2O_5$ under vacuum (~0.1 mmHg) to give crude product (175 g, 97% yield) as a beige powder. The crude product (174 g) was recrystallized from acetonitrile (3.5 L) with charcoal (10 g) decolorization to give 129 g of MPUPA-OSu (2; 68% yield) as a white powder (purity>99%).

mp 211.2–211.8° C.; IR(KBr): 3905–3203 (br band), 1816, 1783, 1654, 1368, 1304, 1244, 1116, 1021 $cm^{-1}$; $^1$H NMR (300 MHz, DMSO-$d_6$): d 9.04 (s, 1 H), 7.92 (s, 1 H), 7.82 (d, 1 H), 7.44 (d, J =8.5 Hz, 2 H), 7.24 (d, J=8.5 Hz, 2 H), 7.15 (m, 2 H), 6.93 (dd, J=7.4, 7.3 Hz, 1 H), 4.02 (s, 2 H), 2.80 (s, 4 H), 2.23 (s, 3 H); MS (EI, ES$^+$) m/z 382 [(M+1)$^+$], 239, 108, 106.

Physical Data for Succinimidyl Boc-(L)-proline (Boc-Pro-OSu, 3; Material Obtained from Bachem Bioscience)

mp 132–136° C.; IR (KBr)3456, 2940, 1731, 1619, 1561, 1541, 1497, 1454, 1395, 1337, 1259, 1202, 1118, 1060 $cm^{-1}$; $^1$H NMR (300 MHz, CDCl$_3$) d 4.51 (dd, J=3.8, 8.7 Hz, 1 H), 3.56 (m, 1 H), 3.44 (m, 1 H), 2.80 (s, 4 H), 2.32 (m, 1 H), 2.27 (m, 1 H), 1.94 (m, 2 H), 1.43 (s, 9 H); MS (EI) m/z 335 (M+N$_2$)$^+$, 279, 213, 138, 114, 86; HPLC 97.1%.

Physical Data for Benzyl-(R)-3-aminobutyrate hemisulfate (4; Material Obtained From Celgene Corp.)

mp 249.4–249.8° C.; IR (KBr) 3515, 3383, 2989, 2945, 2880, 1821, 1788, 1744, 1701, 1476, 1454, 1421, 1394, 1368, 1260, 1241, 1202, 1159, 1077 $cm^{-1}$; $^1$H NMR (300 MHz, CDCl$_3$) d 7.85 (bs, 2 H), 7.26 (s, 5 H), 5.06 (ABq, J=12.3 Hz, 2 H) 4.35 (m, 2 H), 3.73 (m, 1 H), 2.92 (dd, J=6.4, 17.1 Hz, 1 H), 2.66 (dd, J=6.4, 17.0 Hz, 1 H), 1.35 (d, J=6.5 Hz, 3 H); MS (EI) m/z 195 (M+3)$^+$, 194 (M+2)$^+$, 106, 92, 91; HPLC 99.0%.

Preparation of N-(tert-butoxycarbonyl)-L-prolyl-3-methyl-(R)-β-alanine Benzyl Ester (5)

To a well-stirred suspension of benzyl-R-3-aminobutyrate hemisulfate (4; 66.7 g, 213 mmol) in CH$_2$Cl$_2$ (200 mL) were added Boc-(L)-Pro-OSu (3; 53.9 g, 222 mmol) and Et$_3$N (95 mL, 681 mmol). The reaction mixture was allowed to stir at room temperature for 2 h. The reaction mixture was partitioned between EtOAc (1.5 L) and H$_2$O (250 mL) and the organic layer was washed with 10% citric acid (3×250 mL), H$_2$O (250 mL), saturated sodium bicarbonate (250 mL), H$_2$O (250 mL), and brine (3×250 mL), dried over Na$_2$SO$_4$ and concentrated first on the rotavap (40° C.; ~80 mmHg) and then under high-vacuum (room temperature, 16 h; 0.2 mmHg) to provide intermediate 5 as a viscous oil (88.1 g) that contained residual EtOAc and CH$_2$Cl$_2$ (by NMR) and exhibited purity >98% (HPLC). This material was used, without further purification in the reaction below.

$^1$H NMR (300 MHz, CDCl$_3$) d 7.30 (m, 5 H), 6.44 (bs, 1 H), 5.10 (dd, J=12.3, 14.1 Hz, 2 H), 4.32 (m, 1 H), 4.13 (m, 1 H), 3.34 (bs, 2 H), 2.48 (d, J=5.1 Hz, 2 H), 2.1 (m, 2 H), 1.75 (bs, 2 H), 1.40 (s, 9 H), 1.17 (d, J=6.0 Hz, 3 H); MS (EI): m/z 413 [M+Na]$^+$, 313, 291, 191, 194, 165, 91.

Preparation of L-prolyl-3-methyl-(R )-β-alanine Benzyl Ester Hydrochloride (6)

To intermediate 5 from the previous reaction was gradually added a solution of 4 N HCl in dioxane (240 mL). A vigorous evolution of gas ensued (caution: exothermic). The reaction mixture was allowed to stir at room temperature (2 h) and it was then concentrated first on the rotavap (45° C., ~80 mmHg) and then under high-vacuum overnight (room temperature, 14 h, ~0.2 mmHg) to provide an extremely viscous material which was crystallized from CH$_2$Cl$_2$/Et$_2$O (600 mL/700 mL) to provide 64.0 g (92% overall yield for two steps) of the HCl salt 6 as a white solid (HPLC purity 99.6%).

mp 119.8–120.5° C.; IR(KBr): 3217, 3072, 2904, 2756, 1736, 1681, 1560, 1446, 1387, 1352, 1295, 1244, 1178, 1096 $cm^{-1}$; $^1$HNMR (500 MHz, CDCl$_3$) d 10.21 (bs, 1 H), 8.71 (d, J=8.0 Hz, 1 H), 7.77 (bs, 1 H), 7.24 (m, 5 H), 5.00 (s, 2 H), 4.52 (bs, 1 H), 4.22 (apparent t, J=6.5 Hz, 1 H), 3.33 (bs, 2 H), 2.67 (dd, J=5.5, 15.5 Hz, 1 H), 2.44 (m, 2 H), 1.89 (m, 3 H), 1.15 (d, J=6.5 Hz, 3 H); $^{13}$C NMR (125 MHz, CDCl$_3$) d 171.03 (C=O), 167.67 (C=O), 135.58 (C), 128.43 (CH), 128.13 (CH), 128.06 (CH), 66.34 (CH$_2$), 59.71 (CH), 46.55 (CH$_2$), 43.34 (CH), 40.42 (CH$_2$), 30.50 (CH$_2$), 24.23 (CH$_2$), 19.92 (CH$_3$); MS (EI) m/z 291 [M−Cl]$^+$, 199, 194, 160, 139, 92, 91; Anal. Calcd. for C$_{16}$H$_{23}$N$_2$O$_3$Cl: C, 58.80; H, 7.094; N, 8.57; found: C, 58.95; H, 6.99; N, 8.46.

Preparation of N-[[4-[[(2-Methylphenylamino) carbonyl]amino]phenyl]acetyl]-L-prolyl-3-methyl)-(R)-β-Alanine Benzyl Ester (7)

To a solution of the HCl salt 6 (61.77 g, 189 mmol) in DMF (125 mL) was added MPUPA-OSu (2; 69.39 g, 181.9 mmol) followed by Et$_3$N (90 mL; pH ~10). The reaction mixture was allowed to stir 3.5 h and it was then diluted with EtOAc (1 L) and extracted with H$_2$O (3×250 mL). At this point, the product began to precipitate. A 10% solution of citric acid (250 mL) was added to the organic layer (caution: exothermic!), and upon shaking, a copious precipitate formed. The solid was filtered on a sintered-glass funnel (2 L, M). The solid was washed with citric acid (10%, 2×250 mL), H$_2$O (250 mL), satd. Sodium bicarbonate (2×250 mL), H$_2$O (250 mL) and brine (3×250 mL) and allowed to dry on the funnel with suction (~80 mmHg) overnight (~14 h) to provide an off-white solid which was recrystallized from THF/Et$_2$O (1 L/1.4 L) to provide 83.3 g of compound 7 (HPLC purity 99.6%) as a white solid.

The filtrate was further washed with citric acid (10%, 3×250 ml), H$_2$O (250 mL), satd. bicarbonate (2×250 mL), H$_2$O (250 mL) and brine (3×250 mL). With each subsequent aqueous wash, additional compound precipitated out; however washing was continued, care being taken not to lose the precipitate. Filtration provided 4.02 g of the product as a white solid. The filtrate was finally diluted with Et$_2$O (1 L), filtered, and the solid was washed with Et$_2$O (3×100 mL) to provide an additional crop of 1.67 g of the white solid. Total yield for this reaction was 88%.

mp 153–153.5° C.; IR (KBr) 3342, 3307, 3119, 2966, 1737, 1702, 1643, 1590, 1543, 1514, 1455, 1414, 1308, 1238, 1179 $cm^{-1}$; $^1$H NMR (500 MHz, DMSO-$d_6$): a 3:2 mixture of rotamers, (peaks for major conformation): d 9.00

(bs, 1 H), 7.91 (bs, 1 H), 7.84 (d, J=8.3 Hz, 1 H), 7.68 (d, J=8.3 Hz, 1 H), 7.40–7.28 (m, 7 H), 7.13 (3 H), 7.06 (d, J=8.8 Hz, 1 H), 6.92 (t, J=7.3 Hz, 1 H), 5.06 (ABq, J=12.2 Hz, Dn=8.9 Hz, 2 H), 4.18 (dd, J=3.4, 8.8 Hz, 1 H), 4.10 (quintet, J=6.8 Hz, 1 H), 3.57 (m, 2 H), 3.50–3.22 (m, 3 H), 2.62–2.37 (m, 2 H), 2.23 (s, 3 H), 2.18–1.68 (m, 3 H), 1.05 (d, J=6.8 Hz, 3 H) and (peaks for minor conformation): d 9.00 (bs, 1 H), 7.91 (bs, 1 H), 7.84 (d, J=8.3 Hz, 1 H), 8.15 (d, J=8.3 Hz, 1 H), 7.40–7.28 (m, 7 H), 7.13 (3 H), 7.06 (d, J=8.8 Hz, 1 H), 6.92 (t, J=7.3 Hz, 1 H), 5.01 (ABq, J=12.2 Hz, Dn=19.0 Hz, 2 H), 4.32 (dd, J=2.4, 8.8 Hz, 1 H), 4.22 (quintet, J=6.8 Hz, 1 H), 3.57 (m, 2 H), 3.50–3.22 (m, 3 H), 2.62–2.37 (m, 2 H), 2.23 (s, 3 H), 2.18–1.68 (m, 3 H), 1.10 (d, J=6.8 Hz, 3 H); $^{13}$C NMR (125 MHz, DMSO-d$_6$): a mixture of rotamers, (peaks for the major conformation): d 170.80 (C=O), 170.52 (C=O), 169.18 (C=O), 152.61 (C=O), 138.10 (C), 137.38 (C), 136.04 (C), 130.05 (CH), 129.63 (CH), 129.47 (CH), 128.58 (C), 128.28 (CH), 127.89 (CH), 127.85 (C), 126.02 (CH), 122.50 (CH), 117.90 (CH), 117.81 (CH), 65.44 (CH$_2$), 59.61 (CH), 47.04 (CH$_2$), 41.75 (CH), 40.41 (CH$_2$), 40.00 (CH$_2$), 29.29 (CH$_2$), 24.13 (CH$_2$), 19.88 (CH$_3$), 17.78 (CH$_3$) and (peaks for the minor conformation): d 170.94 (C=O), 170.52 (C=O), 169.31 (C=O), 152.61 (C=O), 138.10 (C), 137.38 (C), 136.04 (C), 130.05 (CH), 129.63 (CH), 129.47 (CH), 128.65 (C), 128.28 (CH), 127.89 (CH), 127.85 (C), 126.02 (CH), 120.940 (CH), 117.90 (CH), 117.81 (CH), 65.44 (CH$_2$), 59.91 (CH), 46.51 (CH$_2$), 42.01 (CH), 40.13 (CH$_2$), 39.84 (CH$_2$), 31.75 (CH$_2$), 22.11 (CH$_2$), 20.05 (CH$_3$), 17.78 (CH$_3$); MS (EI): m/z 579 [M+Na]$^+$, 557, 454, 426, 357, 336, 293, 267, 201; Anal. Calcd. for C$_{32}$H$_{36}$N$_4$O$_5$: C, 69.05; H, 6.52; N, 10.07; found: C, 68.87; H, 6.52; N, 9.93.

Preparation of N-[[4-[[(2-Methylphenylamino) carbonyl]amino]phenyl]acetyl]-L-prolyl-3-methyl)- (R)-β-Alanine (8; oMePUPA-V)

A solution of OMePUPA-V-OBn (7; 80.18 g) in THF/H$_2$O (9:1; 800 mL) was hydrogenated at ~55 psi in the presence of Pd/C (10%; 2.44 g). After 25 h, the reaction mixture was filtered through Solka Floc® (144 g; Fiber Sales & Development Corp.) on a sintered-glass funnel. The filtrate was then refiltered through another pad of Solka Floc® (115 g), concentrated to ~250 mL and gradually poured into vigorously stirring toluene (3 L). The suspension was allowed to stir 0.5 h, filtered (2 L sintered glass funnel) and the resultant white powder was allowed to dry, first on the funnel with suction (~80 mmHg; 0.5 h) and then in the vacuum-oven (14 h; 45° C.; pressure adjusted to 25 inHg vacuum with N$_2$ flow). The white lumps were crushed (mortar and pestle) into a fine powder to provide 58.3 g (yield 87%) of oMePUPA-V as a white solid. The product was recrystallized from acetone/H$_2$O (320 mL/75 mL). The crystals were collected and dried first on the sintered glass funnel with suction (1 h, 80 mmHg) and then in the vacuum-oven (25 h; 45° C.; pressure adjusted to 25 inHg-vacuum via N$_2$-flow) to provide 47.0 g (84% recovery from recrystallization) of oMePUPA-V as a white solid (HPLC purity 99.1%).

mp 153.6–154.4° C.; IR (KBr) 3354, 3307, 1719, 1643, 1590, 1543, 1514, 1449, 1414, 1308, 1237 cm$^{-1}$; $^1$H NMR (600 MHz, DMSO-d$_6$): 3:2 mixture of rotamers (peaks for the major conformation): δ 12.21 (bs, 1H), 8.99 (s, 1 H), 7.91 (s, 1 H), 7.87 (d, J=8.2 Hz, 1 H), 7.68 (d, J=7.9 Hz, 1 H), 7.40 (d, J=8.6 Hz, 2 H), 7.17 (d, J=5.9 Hz, 2 H), 7.15 (d, J=7.6 Hz, 1 H), 7.12 (dd, J=7.9, 8.2 Hz, 1 H), 6.94 (dd, J=7.3, 7.3 Hz, 1 H), 4.22 (dd, J=3.3, 8.8 Hz, 1 H), 4.06 (m, J=6.6 Hz, 1 H), 3.47 (dd, 1 H), 3.44 (d, J=15.0 Hz, 1 H), 3.37 (dd, 1 H), 3.29 (d, J=15.4 Hz, 1 H), 2.46 (dd, 1 H), 2.27 (m, 1 H), 2.25 (s, 3 H), 1.99 (m, 1 H), 1.80 m (m, 1 H), 1.78 (m, 1 H), 1.76 (m, 1 H), 1.07 (d, J=6.6 Hz, 3 H) and (peaks for the minor conformation): δ 12.21 (bs, 1 H), 8.99 (s, 1 H), 7.90 (s, 1 H), 7.87 (d, J=8.2 Hz, 1 H), 8.12 (d, J=8.2 Hz, 1 H), 7.40 (d, J=8.6 Hz, 2 H), 7.16 (d, J=5.9 Hz, 2 H), 7.15 (d, J=7.6 Hz, 1 H), 7.12 (dd, J=7.9, 8.2 Hz, 1 H), 6.94 (dd, J=7.3, 7.3 Hz, 1 H), 4.34 (dd, J=1.8, 8.4 Hz, 1 H), 4.18 (m, J=6.6 Hz, 1 H), 3.60 (m, 2 H), 3.59 (m, 1 H), 3.48 (m, 1 H), 2.47 (dd, J=6.6, 15.4 Hz, 1 H), 2.40 (dd, J=6.6, 15.4 Hz, 1 H), 2.25 (s, 3 H), 2.15 (m, 1 H), 1.83 (m, 1 H), 1.91 (m, 1 H), 1.77 (m, 1 H), 1.12 (d, J=6.6Hz, 3 H); $^{13}$C NMR (150 MHz, DMSO-d$_6$) (peaks for the major conformation): δ 172.4 (C=O), 170.9 (C=O), 169.3 (C=O), 152.6 (C=O), 138.2 (C), 137.5 (C), 130.2 (CH), 129.8 (CH), 129.6 (CH), 128.7 (C), 127.4 (C), 126.1 (CH), 122.6 (CH), 120.9 (CH), 118.0 (CH), 117.9 (CH), 59.7 (CH), 46.6 (CH$_2$), 41.7 (CH$_2$), 40.6 (CH$_2$), 40.2 (CH$_2$), 29.4 (CH$_2$), 22.2 (CH$_2$), 19.9 (CH$_3$), 17.9 (CH$_3$) and peaks for the minor conformation): δ 172.5 (C=O), 171.0 (C=O), 160.5 (C=O), 152.7 (C=O), 138.19 (C), 137.5 (C), 130.2 (CH), 129.8 (CH), 129.6 (CH), 128.8 (C), 127.4 (C), 126.1 (CH), 122.6 (CH), 120.9 (CH), 118.0 (CH), 117.9 (CH), 59.9 (CH), 47.1 (CH$_2$), 42.0 (CH$_2$), 39.8 (CH$_2$), 40.3 (CH$_2$), 31.8 (CH$_2$), 24.2 (CH$_2$), 20.2 (CH$_3$), 17.9 (CH$_3$); MS (EI) m/z 468 [M+H]$^+$, 336, 267, 137; Anal. Calcd. for C$_{25}$H$_{30}$N$_4$O$_5$: C, 64.36; H, 6.48; N, 12.01; found: C, 64.07; H, 6.40; N, 11.85.

Example 2

Activity in an Ovine Model of Allergic Pulmonary Inflammation

Allergic sheep weighing between 27–50 kg were used. All sheep had previously been shown to develop both early and late bronchial responses to inhaled nebulized *Ascaris suum* allergen. The sheep were conscious and were restrained in a modified shopping cart in the prone position with their heads immobilized. After topical anesthesia of the nasal passages with 2% lidocaine, a balloon catheter was advanced through one nostril into the lower esophagus. The animals were intubated with a cuffed endotracheal tube through the other nostril using a flexible fiberoptic bronchoscope as a guide. All protocols used in this study were approved by the Mount Sinai Medical Center Animal Research Committee, which is responsible for assuring the humane care and use of experimental animals. Pleural pressure was estimated using an esophageal balloon catheter (filled with 1 mL of air), which was positioned 5 to 10 cm from the gastroesophageal-junction. In this position, the end expiratory pleural pressure ranged between −2 to −5-cmH$_2$O. Once the balloon was placed, it was secured so that it remained in the same position for the duration of the experiment. Lateral pressure in the trachea was measured with a sidehole catheter (inner diameter, 2.5 mm) advanced through and positioned distal to the tip of the endotracheal tube.

The tracheal and pleural pressure catheters were connected to a differential pressure transducer (MP45, Validyne, Northridge, Calif.) for the measurement of transpulmonary pressure which was defined as the difference between tracheal and pleural pressure. Airflow was measured by connecting the proximal end of the endotracheal tube to a pneumotachograph (Fleisch, Dyna Sciences, Inc., Blue Bell, Pa.). The signals of transpulmonary pressure and flow were recorded on a multichannel physiological recorder which was linked to a 80–386 DOS Personal Computer for on-line calculation of mean pulmonary flow resistance ($R_L$) by dividing the change in transpulmonary pressure by the change in flow at mid-tidal volume (obtained by digital integration). The mean of at least five breaths, free of swallowing artifact, was used to obtain $R_L$ in cmH$_2$O/L/sec. Immediately after the measurement of $R_L$, thoracic gas volume ($V_{tg}$) was measured in a constant-volume body plethysmograph to obtain specific lung resistance (SR$_L$=R$_L$× V$_{tg}$) in L×cmH$_2$O/L/sec.

All liquid-dose aerosols were generated using a disposable medical air-jet nebulizer (Raindrop®, Puritan Bennett, Lenexa, Kans.) that provided an aerosol with a mass median aerodynamic diameter of 3.2 μm as determined by an Andersen cascade impactor. The nebulizer was connected to a dosimeter system, consisting of a solenoid valve and a source of compressed air (20 psi). The output of the nebulizer was directed into a plastic T-piece, one end of which was connected to the inspiratory port of a piston respirator (Harvard Apparatus, S. Natick, Mass.). The solenoid valve was activated for one second at the beginning of the inspiratory cycle of the respirator. Aerosols were delivered at a tidal volume of 500 mL and a rate of 20 breaths per minute. To assess bronchial responsiveness, cumulative concentration response curves to carbachol were performed by measuring SR$_L$ immediately after inhalation of buffer and after each consecutive administration of 10 breaths of increasing concentrations of carbachol (0.25, 0.5, 1.0, 2.0 and 4.0% w/v in buffered saline). The provocation test was discontinued when SR$_L$ increased over 400% from the post-saline value or after the highest carbachol concentration had been administered. Bronchial responsiveness was assessed by determining the cumulative carbachol concentration (in breath units) that increased SR$_L$ by 400% over the post-saline value (PC$_{400}$) by interpolation from the dose response curve. One breath unit (BU) was defined as one breath of a 1% w/v carbachol nebulized solution.

Doses of oMePUPA-V were dissolved in either ethanol::normal saline 1:2, ethanol:200 mM sodium phosphate 1:5 or Tris buffer. When using Tris, any required dilution was performed using normal saline. Doses were prepared in 3–5 mL total volume.

Values are expressed as means ± standard error of the mean. Change in SR$_L$ was calculated for each sheep as the difference from pre-challenge baseline SR$_L$. Post-challenge changes in SR$_L$ were characterized by an early airway response (EAR) which evolved over the approximately 0–4-hour period. This was followed by a late airway response (LAR) that evolved over the approximately 4–8-hour period after allergen challenge. Areas under the EAR and LAR curves were computed for each animal using the trapezoidal rule. Significant reductions in area under the EAR or LAR curves compared to placebo control were taken to be therapeutic effects on allergen-induced changes in SR$_L$. Airway responsiveness to carbachol (PC$_{400}$) assessed before, and at 24 h after allergen challenge, was expressed as a PC$_{400}$ ratio (post/prechallenge PC$_{400}$ values) for each sheep. A significant increase in the PC$_{400}$ ratio compared to placebo control was taken to be a therapeutic effect. Comparisons to placebo control were made using one-way analysis of variance followed by Dunnett's test (1-tailed) for multiple comparison to a control. Comparisons that resulted in p<0.05 were taken to be statistically significant.

FIG. 1 shows aerosolized oMePUPA-V's inhibitory dose-response in *Ascaris suum*-sensitive sheep challenged 2 h after dosing. Left panels display change in specific lung resistance SR$_L$, cm H$_2$O/sec. Right panels display airway responsiveness to inhaled carbachol (PC$_{400}$ ratio, pre/post-challenge) determined at 24 h after challenge. oMePUPA-V at doses of 0.01 and a 0.03 mg did not inhibit early or late airway response or alter hyperresponsiveness to carbachol at 24 h after allergen challenge. Doses of 0.1, 1 and 3 mg inhibited the early airway response and maximally inhibited the late airway response. These doses also inhibited the hyperresponsiveness to carbachol at 24 h after allergen challenge. The statistical analysis of this data is shown in Table 2.

TABLE 2

| Treatment | Dose (mg) | Vehicle | n | EAR (ΔSLR × h) | LAR (ΔSLR × h) | PC$_{400}$ (Post/Pre) |
|---|---|---|---|---|---|---|
| Dosed 2 Hours prior to Allergen Challenge | | | | | | |
| PBS | | | 12 | 5.85 ± 0.62 | 4.85 ± 0.69 | 0.49 ± 0.03 |
| oMePUPA-V | 0.01 | EtOH:NS | 2 | 6.87 ± 0.05 | 5.11 ± 1.46 | 0.44 ± 0.04 |
| | 0.03 | EtOH:NS | 2 | 10.62 ± 3.91 | 3.98 ± 0.23 | 0.43 ± 0.00 |
| | 0.10 | EtOH:NS | 4 | 2.54 ± 0.74* | 0.67 ± 0.17* | 1.18 ± 0.11* |
| | 1.00 | EtOH:PBS | 2 | 2.14 ± 0.70 | 0.27 ± 0.34* | 1.05 ± 0.11* |
| | 3.00 | EtOH:PBS | 2 | 2.47 ± 0.62 | 0.68 ± 0.07* | 1.07 ± 0.08* |

In all studies, baseline airway responsiveness (i.e., PC$_{400}$) was determined three to four days before initiating a study. In single-dose pre-treatment studies, SR$_L$ was measured and animals were treated with the compound or with vehicle. SR$_L$ was remeasured 2 hours after treatment Oust before challenge) and then the animals were challenged with allergen. In multiple-dose studies, beginning 4 days before allergen challenge, animals were treated once-daily for 4 days and challenged with allergen 24 h after the last dose. SR$_L$ was measured before and after the last dose of compound or vehicle treatment. In all studies, SR$_L$ was remeasured immediately after allergen challenge, hourly from 1–6 hours after challenge, and half-hourly from 6.5–8 hours after allergen challenge. Post-challenge determinations of airway responsiveness (PC$_{400}$) were made 24 hours after allergen challenge.

Sheep, naturally sensitive to *Ascaris suum*, were challenged with an aerosol of *Ascaris suum* allergen 2 h after aerosol administration of oMePUPA-V at the doses indicated or 24 h after the last dose of repeated daily administration for 4 days of a subthreshold dose of oMePUPA-V or the equivalent amount of PBS. Pulmonary mechanics, reported as the change in specific airways resistance from the pre-study baseline value, were measured for 8 hours post-allergen challenge. Early Airway Response (0–4 h, EAR) and Late Airway Response (4–8 h, LAR) are expressed as the mean area under the Δ Specific Lung Resistance curve verses time ± s.e.m. Airways resistance to inhaled carbachol was determined prior to study initiation and at 24 h post-allergen challenge. Airways responsiveness is reported as the PC$_{400}$ (amount of carbachol required to increase resistance by 400%) ratio by comparison of pre-challenge and post-challenge values.

*=p<0.05 compared to PBS control, one-way analysis of variance, followed by Dunnett's test for multiple comparison to a control group. Indicates a statistically significant decrease in EAR or LAR, or a significant increase in $PC_{400}$ ratio compared to PBS control group.

Single Dose Irritancy

Figure 2:
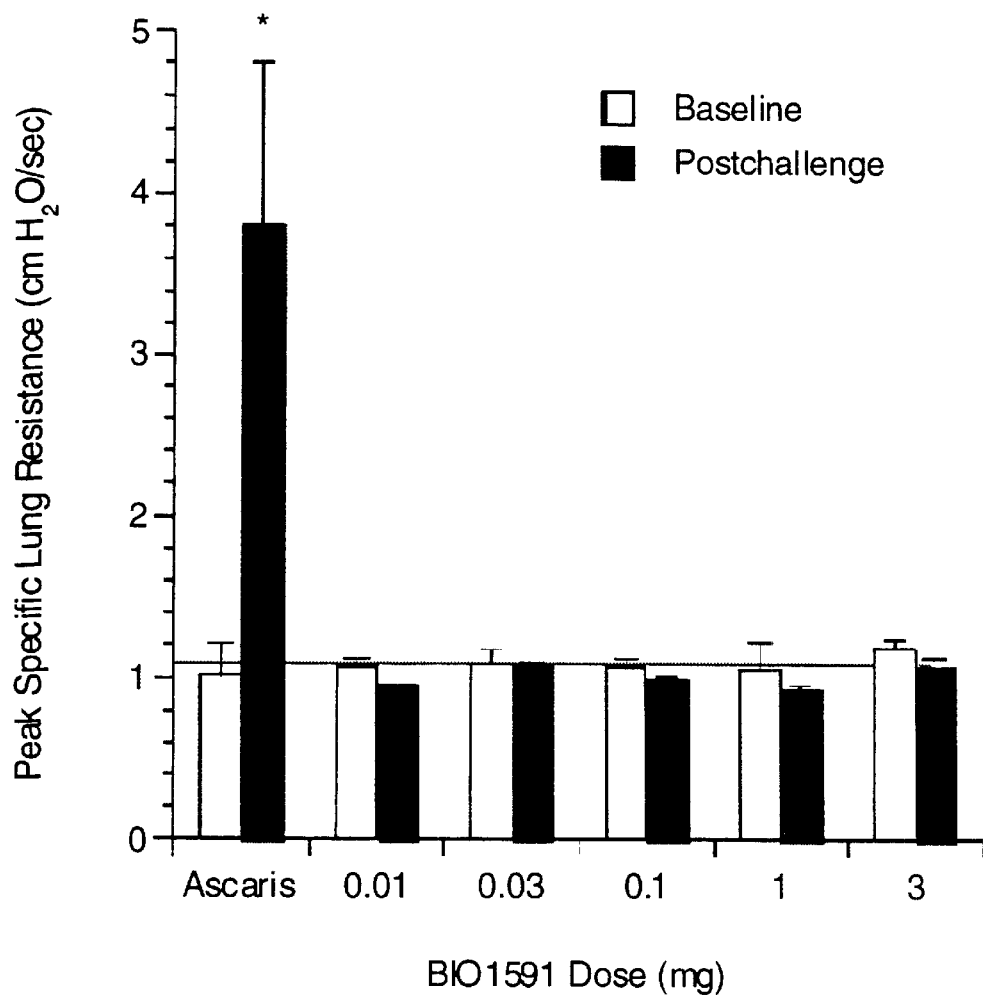
FIG. 2: Sheep, naturally sensitive to Ascaris suum, were challenged with an aerosol administration of oMePUPA-V at the doses indicated or an aerosol of *Ascaris suum*. Changes in airways resistance were measured following aerosol challenge and peak specific lung resistance (cm $H_2O$/sec) after challenge was compared to baseline values. *=p<0.05 compared to PBS control, one-way analysis of variance, followed by Dunnett's test for multiple comparison to a control group. Indicates a statistically significant increase in peak specific lung resistance compared to PBS control group.

None of the doses of oMePUPA-V used in the above study had an irritant effect, as reflected by the lack of change in airways resistance compared to baseline resistance, following challenge with *Ascaris suum* allergen. This is shown in FIG. 2.

Repeated Dose Studies

Figure 3:
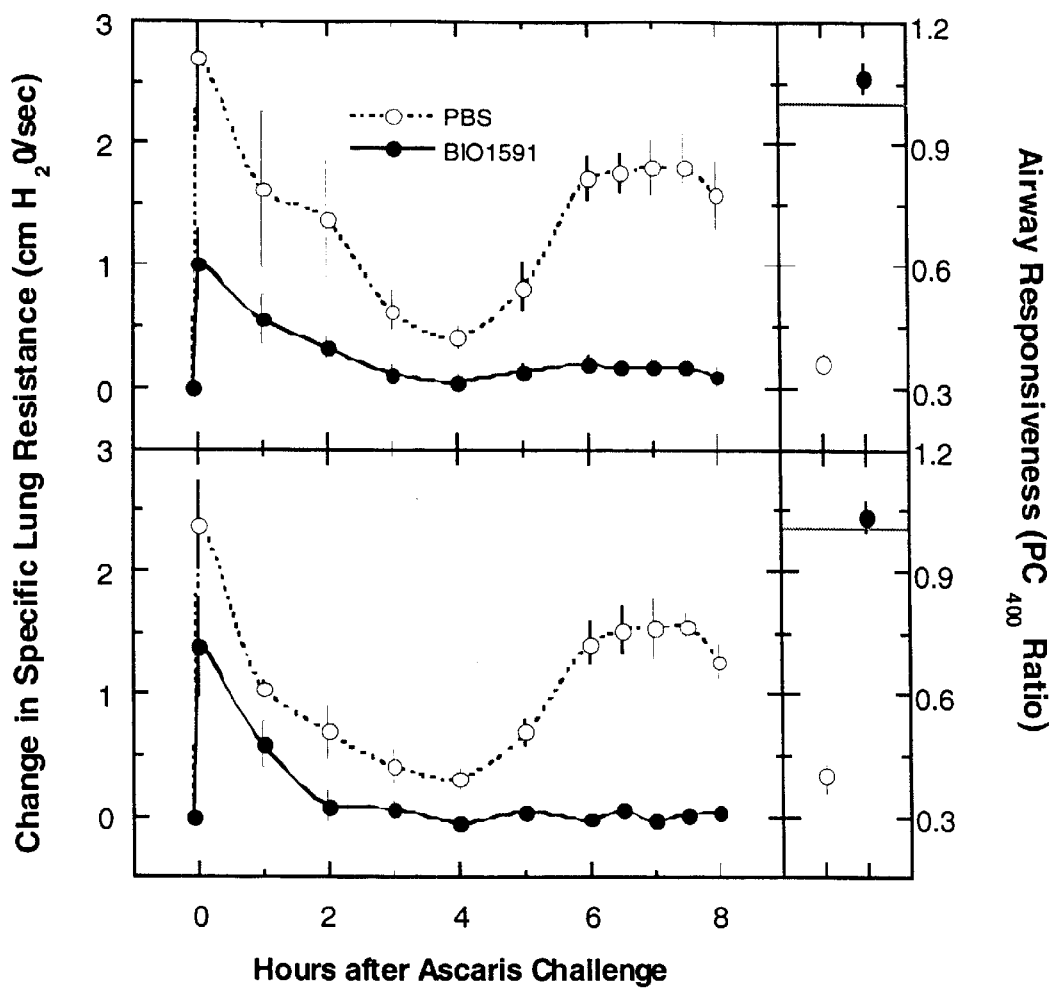
FIG. 3 Sheep, naturally sensitive to Ascaris suum, were challenged with an aerosol of *Ascaris suum* allergen 24 h after the fourth daily aerosol administration of oMePUPA-V (0.03 mg) or an equivalent amount of vehicle (ethanol:normal saline, 1:2, upper panel; Tris:normal saline, 1:499, lower panel). Pulmonary mechanics were measured at the indicated times and are reported as the change in specific airways resistance from the pre-study baseline value (left panels). Airways resistance to inhaled carbachol was determined prior to study initiation and at 24 h post-allergen challenge (right panels). Airways responsiveness is reported as the $PC_{400}$ (amount of carbachol required to increase resistance by 400%) ratio by comparison of pre-challenge and post-challenge values.

FIG. 3 illustrates that a 0.03 mg dose of oMePUPA-V, which was shown to be ineffective when used as a single dose acute pretreatment, was nevertheless protective if given once daily for 4 days, when antigen challenge was given 24 h after the last dose. The upper and lower left hand panels show that this effect was seen using two different formulations. Hyperresponsiveness to carbachol after a further 24 h was also maximally inhibited as shown in the upper and lower right hand panels of FIG. 3. The protective effect of oMePUPA-V was significant against EAR and LAR and against hyperresponsiveness to carbachol and the quantitative analysis is shown in Table 3.

The results of this study indicate that a single pretreatment with a small molecule inhibitor of VLA-4, oMePUPA-V, by aerosol, can protect against allergen-induced early and late airways responses and post allergen-induced AHR in the allergic sheep model. No irritant effect on airways was seen with any of the doses of oMePUPA-V given as a single pretreatment. Results also showed that the effective dose of oMePUPA-V could be reduced with multiple treatments. Collectively these data provide strong evidence that the VLA-4 adhesion pathway plays a critical role in the pathophysiologic indicators (LAR and AHR) of the prolonged inflammatory events that are initiated in the airways of allergic sheep following allergen provocation.

TABLE 3

| Treatment | Dose (mg) | Vehicle | n | EAR (ΔSLR × h) | LAR (ΔSLR × h) | $PC_{400}$ (Post/Pre) |
|---|---|---|---|---|---|---|
| Dosed Once Daily for 4 Days, Challenge Given 24 h after Last Dose ||||||||
| PBS | | | 8 | 4.33 ± 0.81 | 4.96 ± 0.40 | 0.38 ± 0.03 |
| oMe-PUPA-V | 0.03 | EtOH: NS | 4 | 1.53 ± 0.34* | 0.59 ± 0.16* | 1.06 ± 0.04* |
| | 0.03 | Tris: NS | 4 | 1.40 ± 0.35* | 0.02 ± 0.06* | 1.04 ± 0.04* |

Sheep, naturally sensitive to *Ascaris suum*, were challenged with an aerosol of *Ascaris suum* allergen 24 h after the last dose of repeated daily administration for 4 days of a subthreshold dose of oMePUPA-V or the equivalent amount of PBS. Pulmonary mechanics, reported as the change in specific airways resistance from the pre-study baseline value, were measured for 8 hours post-allergen challenge. Early Airway Response (0–4 h, EAR) and Late Airway Response (4–8 h, LAR) are expressed as the mean area under the Specific Lung Resistance curve verses time ± s.e.m. Airways resistance to inhaled carbachol was determined prior to study initiation and at 24 h post-allergen challenge. Airways responsiveness is reported as the $PC_{400}$ (amount of carbachol required to increase resistance by 400%) ratio by comparison of pre-challenge and post-challenge values.

*=p<0.05 compared to PBS control, one-way analysis of variance, followed by Dunnett's test for multiple comparison to a control group. Indicates a statistically significant decrease in EAR or LAR, or a significant increase in $PC_{400}$ ratio compared to PBS control group Example 3

Activity in Models of Delayed Type Hypersensitivity

Sheep Red Blood Cell Studies

Specific pathogen-free female Balb/c mice, aged 8–10 weeks, from Jackson Labs were used for all experiments. The animals were fed food and water ad libitum. Sheep red blood cells (sRBC) in Alsever's solution from the same sheep were obtained weekly from Charles River Pharm. Services (Southbridge, Mass.). The sRBC were pelleted by centrifugation at 1000 g for 10 minutes at 4° C. and any visible buffy coat removed. The cells were then washed in saline. The cell pellet was resuspended in saline and counted using a hemocytometer. The cells were diluted in phosphate buffered saline (PBS) to $2 \times 10^8$ sRBC per mL. On Day 0, mice were sensitized by a s.c. injection of $2 \times 10^7$ sRBC in 100 μL PBS. On Day 5, sRBC were prepared as above, but diluted in PBS to a final concentration of $4 \times 10^9$ sRBC per ml. Of this preparation, 25 μL was injected s.c. into the right rear footpad.

For enteral administration of compound, oMePUPA-V (Lot #2770-029) was formulated in a vehicle of 60% PEG 400 in 0.02M TRIS to a stock concentration of 5 mg/mL. Appropriate dilutions were prepared in the PEG/TRIS vehicle and administered enterally in a volume of 100 μL. The anti-VLA-4 antibody (PS/2) was diluted in saline at a concentration of 4.3 mg/kg and administered intraperitoneally in 100 μL. All treatments were administered immediately following challenge with sRBC.

Swelling of unchallenged control (left) and challenged (right) rear footpads was measured using a tension caliper from Mitutoyo (Model #304-196, Dyer, Lancaster, Pa.) at 20 hours post-footpad challenge. The data are presented as the change in footpad thickness, determined by subtracting the left hind paw thickness from the right hind paw thickness. Changes in footpad thickness were compared using a two-tailed Student's t-test.

The anti-VLA-4 antibody PS/2 at a dose of 4.3 mg/kg intraperitoneally inhibited swelling by approximately 30% whereas oMePUPA-V administered enterally at a dose of 20 mg/kg was without effect in this model (data not shown). The efficacy of oMePUPA-V administered at a dose of 20 mg/kg by the enteral route in the sRBC-induced DTH model in mice was studied and no efficacy was observed.

Example 4

Activity in Models of Delayed Type Hypersensitivity

Contact Hypersensitivity Model

Figure 4:
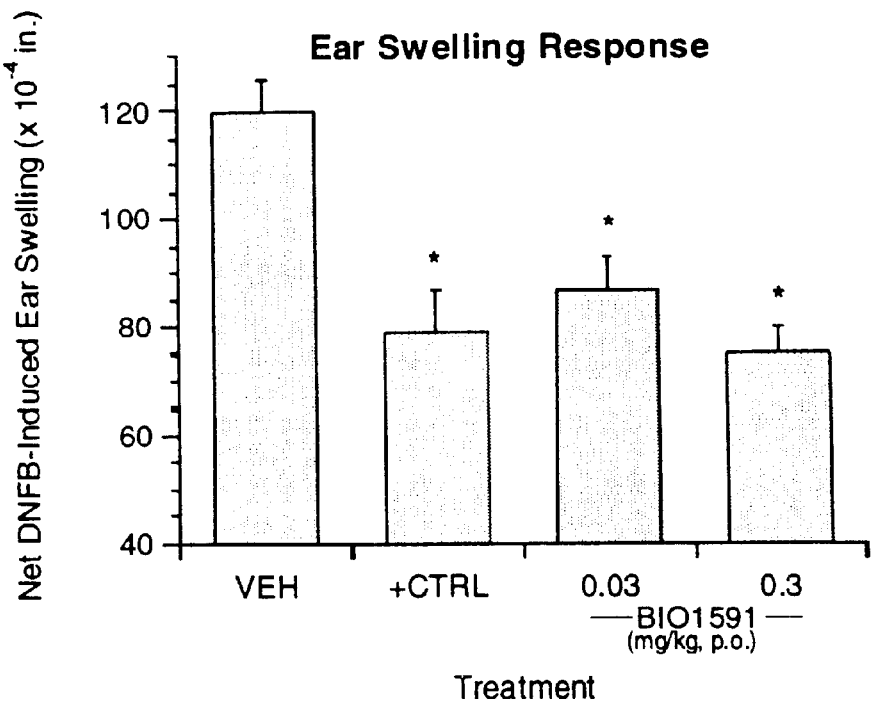
FIG. 4. Balb/c mice, previously sensitized to DNFB, were challenged by application of DNFB to the dorsal surface of the left ear and vehicle to the dorsal surface of the right ear. Twenty-four hours later the thickness of the ears was measured with a micrometer. oMePUPA-V was administered at the indicated doses 4 hours after challenge with DNFB. Positive control (+CTRL) compound was given at a maximally effective enteral dose. Values are means ± standard error of the mean for 8 animals. Upper panel shows absolute ear swelling. Lower panel shows percent inhibition of ear swelling compared to vehicle (VEH) control.
Figure 4:
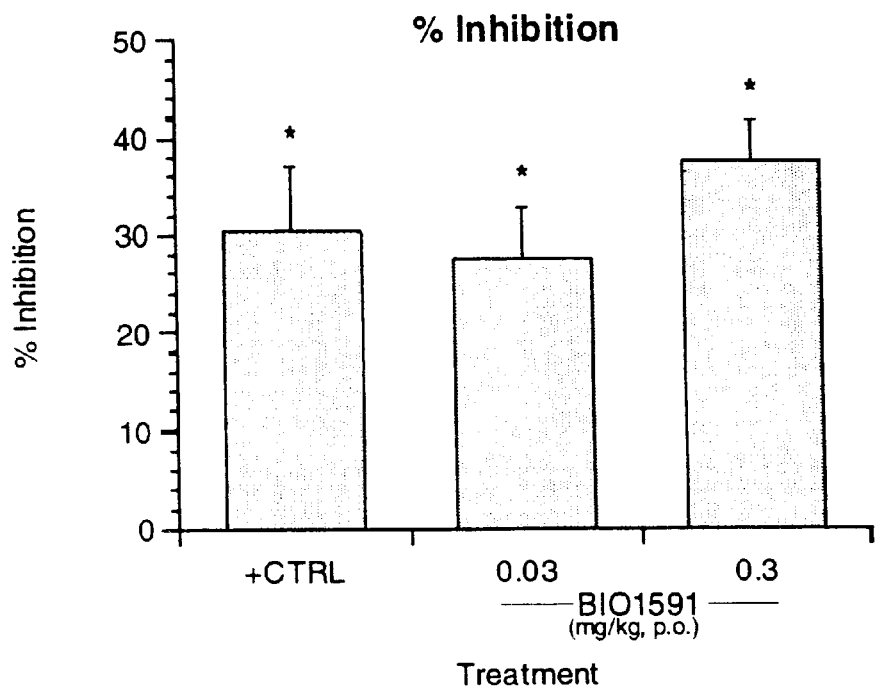

Twenty gram female virus-free Balb/c mice (Jackson Laboratories, Bar Harbor, Me.) housed four to a cage in microisolator cages in Biogen's virus-free animal facility and receiving ad libitum mouse chow and tap water were used for all studies. Mice were anesthetized with ketamine:xylazine (90:10 mg/kg, i.p.). A 3 cm² patch of abdominal skin, xiphoid to pubis was exposed by closely shaving the far and the skin was scrubbed with 70% ethanol. A 25 μL volume of 0.5% DNFB in 4:1 v/v acetone:olive oil vehicle is uniformly applied to the bare abdominal skin. The skin was lightly scratched with the applying pipette tip to encourage mild inflammation. The mouse was laid supine in its cage and allowed to recover from anesthesia. Twenty four hours after the initial sensitization, mice were again sensitized with 25 μL of 0.5% DNFB in vehicle at the same abdominal skin location, again followed by light scratching with the pipette tip. The second sensitization was performed while restraining the unanesthetized mouse. On Day 5 (approximately 120 hours after the initial sensitization), a subirritant dose of the sensitizer (0.2% DNFB in 4:1 v/v acetone:olive oil vehicle) was used to challenge the immune response. Mice were anesthetized with 90:10 mg/kg ketamine:xylazine, i.p. and 10 μL of 0.2% DNFB was applied to the dorsal surface of the left ear. The right ear received a similar application of the 4:1 v/v acetone:olive oil vehicle. Over the subsequent 24 hour period, a biphasic ear swelling response evolved, as shown in FIG. 4. Twenty four hours after challenge, mice were again anesthetized with ketamine:xylazine and the ear thickness of both ears measured with an engineer's micrometer to an accuracy of $10^{-4}$ inches.

Compounds (100 μL) or appropriate vehicle (Dimethylsulfoxide [DMSO] in isotonic phosphate buffered saline [PBS], 100 μL) were administered orally by gavage 4 hours after challenging the immune response on Day 5. Groups of 8 mice were used for each treatment tested. oMePUPA-V (Batch Number 2044-076) was dissolved in distilled water by the addition of 0.5% sodium phosphate buffer, pH 8.8, and 3% DMSO. The ear swelling response for each mouse was calculated as the difference between its vehicle- and DNFB-challenged ear thickness at 24 hours after challenge. Typical DNFB-induced ear swelling was 65–75×$10^{-4}$ inches. Inhibition of the ear swelling response was determined by comparison of treated groups with their vehicle control group. Statistical significance of the difference among treatment groups was evaluated using one-way analysis of variance followed by Dunnett's test for multiple comparisons to a control group (Systat, SPSS Inc.) using $p<0.05$. Values are expressed as means ± standard error of the mean (SEM).

FIG. 4 compares ear swelling responses measured 24 hours after DNFB challenge in mice that received vehicle (DMSO, PBS), positive control compound (given at 0.03 μg/kg), or 0.03 or 0.3 mg/kg oMePUPA-V, dosed enterally 4 hours after DNFB challenge (upper panel). Treatment-induced percents inhibition are shown in the lower panel. Both doses of oMePUPA-V significantly inhibited the ear swelling response to an extent similar to that shown by the positive control compound.

Single enteral 0.03 or 0.3 mg/kg doses of oMePUPA-V given 4 hours after DNFB challenge can significantly inhibit the ear swelling response in a model of mouse contact hypersensitivity.

Example 5

Biochemistry 5.1 Receptor Affinity of oMePUPA-V as Measured Using VCAM-Ig Alkaline Phosphatase Conjugate in VCAM-Ig Direct Binding Assay (DBA)

VCAM-Ig was constructed and purified as published (Jakubowski, A. et al. Cell Adhesion and Communication 3:131–142, 1995). Conjugation to calf intestinal alkaline phosphatase, for purposes of cleaving a chromogenic substrate, was performed as published (Lobb, R. R. et al. Cell Adhesion and Communication 3:385–397, 1995). Binding to VLA-4 was assessed on the human T cell line, Jurkat (α4β1). VCAM-Ig-AP and oMePUPA-V competed for binding to α4β1 on the surface of these cells in the presence of 1 mM $Mn^{+2}$ In the VCAM-Ig Direct Binding Assay, oMePUPA-V competes with VCAM-Ig-AP for binding to Jurkat cells in the presence of 1 mM $MnCl_2$, concentration-dependently, with an $IC_{50}$ of 8±1 nM (n=9). Results are shown in Table 4.

5.2 Receptor affinity of oMePUPA-V as measured using VCAM-Ig Alkaline Phosphatase Conjugate in the Purified VLA-4 Protein/Protein Assay VLA-4 was purified from a detergent extract of a high expressing subclone of α4-transfected K562 cells by antibody affinity chromatography and immobilized on microtiter wells to establish a protein/protein competitive binding assay. VCAM-Ig-AP was bound to the purified VLA-4-coated plate in the absence or presence of oMePUPA-V (Lot #2) and 1 mM $MnCl_2$. Plates were read at 405 nm and the data were analyzed using SoftMax v. 2.32 software.

Binding of the VCAM-Ig conjugate to purified VLA-4 was blocked completely by a specific neutralizing anti-α4 monoclonal antibody (HP1/2). Two $IC_{50}$'s obtained for oMePUPA-V in the VLA-4 Protein/Protein Assay are tabulated in Table 4 as are the $IC_{50}$'s obtained on Jurkat cells from the VCAM-Ig-AP Competitive Binding Assay and CS1 Cell Adhesion Assay.

5.3 Receptor Affinity of oMePUPA-V as Assessed in the CS1 Cell Adhesion Assay a. Adhesion of Jurkat Cells to CS1/BSA Conjugate The peptide $NH_2$-cysteine-tyrosine-CS-1 was synthesized and coupled to BSA-SMCC (SMCC is a heterobifunctional crosslinker which reacts with free amino groups on BSA and the sole cysteine of the synthetic peptide) at a CS1/BSA ratio of 10:1. Wells were coated overnight with 100 μL of conjugate diluted to a final concentration of 1 ug/ml. The next day the wells were blocked with BSA in PBS for one hour and then washed three times.

The human T cell line, Jurkat, was labeled with 2 μM BCECF-AM, a fluorescent dye (2', 7', bis-(2-carboxyethyl)-5 and -6) carboxy fluorescein acetoxymethyl ester (Molecular Probes Inc., Eugene, Oregon; catalog #B-1150) that is internalized and deesterified thus trapping the dye within live cells. Jurkat cells (1×$10^5$ cells/well) in buffer containing 1 mM $Mn^{+2}$ were added to the coated plates in the presence of three-fold serial dilutions of inhibitor. Each concentration was assayed in duplicate. After 30 minutes at room temperature, the plates were inverted and washed three times or until no cells were adherent to control wells coated with BSA alone. CS1-adherent cells were quantitated in a Cytofluor fluorescent platereader using an excitation wavelength of 485 nm and an emission wavelength of 530 nm.

Cells adhered to CS1/BSA in the absence of compound served as the 0% inhibition control whereas cells adhering to BSA alone served as the 100% inhibition control. IC50's were calculated using Deltagraph software, version 5.

Adhesion of labeled Jurkat cells in the presence of $Mn^{+2}$ was blocked completely by EDTA and the neutralizing anti-α4β1 mAb, HP1/2, indicating that binding was specific. Table 4 gives the activity of oMePUPA-V in the CS1/BSA adhesion assay, as well as the binding assay results.

oMePUPA-V is a potent VLA-4 antagonist in buffers containing $Mn^{+2}$. It is 80-fold more potent when assayed in the presence of $Mn^{+2}$ on isolated VLA-4 than on Jurkat cells in the binding assay. oMePUPA-V is a functional antagonist as revealed by its ability to dose-dependently and completely block adhesion of Jurkat to CS1. The absolute values in the adhesion assay are greater than those observed in the binding assays. This may be due to the multivalent nature of adhesion. In all assay formats, inhibition of binding by EDTA and HP1/2 demonstrate specific binding to VLA-4.

TABLE 4

Receptor affinity of oMePUPA-V in the presence of 1 mM $MnCl_2$ as measured in VCAM-Ig Competitive Binding Assay, the CS1 cell adhesion assay and purified VLA-4 Protein/Protein Assay

| Assay | $IC_{50}$ ± SD [nM] oMePUPA-V |
|---|---|
| Jurkat cell VCAM-Ig Binding | 8 ± 1 (n = 9) |
| Jurkat cell CS1 adhesion | 22 ± 2 (n = 4) |
| Purified VLA-4 VCAM-Ig binding | 0.1 (n = 2) (0.1, 0.1) |

6.4 Specificity of oMePUPA-V Inhibition a. Specificity of oMePUPA-V as Assessed Using JY Cells in the VCAM-Ig Direct Binding and CS1 Adhesion Assays Binding to α4β7 was assessed on JY cells in the presence of $Mn^{+2}$. In the binding assay, VCAM-Ig and oMePUPA-V compete for binding to α4β7 on JY cells (See section 4.1.1 for assay protocol). In the cell adhesion assay, oMePUPA-V was tested for its ability to block JY (α4β7) cell binding to CS1/BSA conjugate oMePUPA-V does not block α4β7 binding to VCAM-Ig or CS1/BSA. The anti-β7 Mab, Fib27 (Pharmingen), inhibited these interactions completely indicating that binding was α4β7 specific. Therefore oMePUPA-V is a specific inhibitor for VLA-4. Results are tabulated in Table 5.

b. Specificity of oMePUPA-V as Assessed Using Adhesion of K562 Cells to Wells Coated with Fn-120

Untreated 96 well polystyrene flat bottom plates were coated with 5 μg/ml Fn-120 overnight at 4° C. The plates were washed twice with phosphate buffered saline (PBS) and blocked with 1% Bovine Serum Albumin (BSA) for 1 hour at room temperature. The plates were washed twice with TBS buffer containing 1 mM $MnCl_2$ (assay buffer). K562 cells were labeled with 2 μM of the fluorescent dye, BCECF-AM (see section 4.1.3), and bound to the plate for 30 minutes at room temperature. The plates were inverted and washed three times and adherent cells were quantitated in a Cytofluor fluorescent platereader using an excitation wavelength of 485 nm and an emission wavelength of 530

Adhesion of K562 to Fn-120 was completely blocked by the neutralizing anti-α5 antibody, IIA1 (Pharmingen), indicating specific binding through VLA-5. There was no inhibition of K562 cell binding to the Fn120K fragment by oMePUPA-V in doses as high as 100 μM. See Table 5 below.

c. Aggregation Assays Performed to Assess the Specificity of oMePUPA-V Methods

Activity against gpIIbIIIa was assessed by means of standard platelet aggregometry using platelet rich plasma. ADP was used to initiate aggregation in the presence of plasma where $Ca^{+2}$ and $Mg^{+2}$ are the major divalent cations. GRGDSP @ 100 ug/mL was used as a positive control.

Results oMePUPA-V was tested at three doses 1, 10 and 100 μM. It did not inhibit platelet aggregation as induced by ADP, at any dose. Results are listed in Table 5. oMePUPA-V is highly (>10,000 fold) specific for VLA-4. It has no measurable activity (>100 μM) against the related integrins, α4β7 and VLA-5 or against the β3 integrin, gpIIbIIIa.

TABLE 5

Inhibitory activity of oMePUPA-V as measured in the α4β7 VCAM-Ig Competitive Binding Assay, α4β7 and VLA5 adhesion assays, and in the platelet aggregation studies

| Cell Line | Ligand | Divalent Cation | oMePUPA-V $IC_{50}$ ± SD [nM] |
|---|---|---|---|
| JY (α4β7) | VCAM-Ig DBA | $Mn^{+2}$ | 3% inhibition @ 100 μM (n = 3) |
| JY (α4β7) | CS1/BSA adhesion | $Mn^{+2}$ | no inhibition @ 100 μM (n = 4) |
| K562 (VLA-5) | Fn-120 adhesion | $Mn^{+2}$ | no inhibition @ 100 μM (n = 3) |
| platelets (IIbIIIa) | fibrinogen aggregation | $Ca^{+2}/Mg^{+2}$ | no inhibition @ 100 μM (n = 1) |

Example 6

Assay of oMePUPA-V for LIBS Induction 6.1. Measurement on Jurkat Using LIBS Antibody 9EG7 a. LIBS Induction by α4β1 Antagonists was Assayed in vitro by FACS Analysis.

Jurkat cells ($2 \times 10^5$/well) were preincubated at 37° C. for 20 minutes with TRIS-buffered saline containing 2 mM $MgCl_2$ ($Mg^{+2}$-TBS) alone or with serial dilutions of test compounds. The samples were transferred to an ice bath and supplemented with LIBS antibody, 9EG7, at a final concentration of 10 μg/ml. The cells were washed twice with $Mg^{+2}$-TBS and resuspended in a 1:200 dilution of a FITC conjugated-goat anti-rat IgG in $Mg^{+2}$-TBS and incubated for 30 min at 4° C. The cells were washed twice and resuspended in $Mg^{+2}$-TBS. Mean fluorescence intensity (MFI) was determined by FACS analysis (Becton Dickinson FACScan). Results are expressed as MFI. Data were analyzed by Microsoft Excel v5.0 and Deltagraph v4.0 software.

Figure 5:
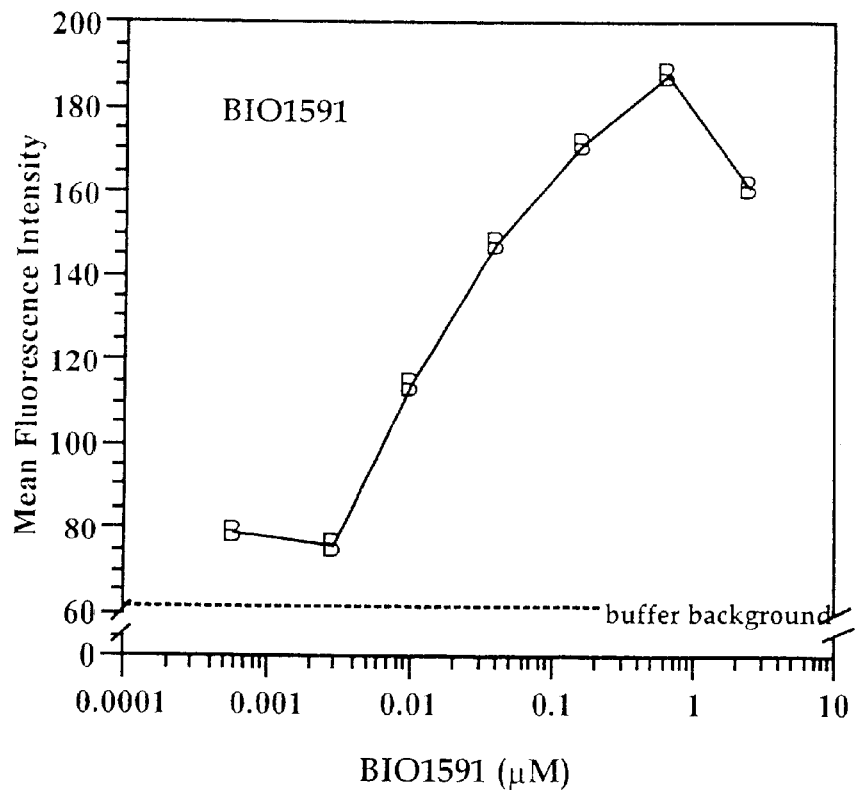
FIG. 5. Analysis of competition between OMePUPA-V and a known inhibitor under various conditions of activation. Jurkat cells ($1.5 \times 10^6$/ml) in TBS plus 2 mM $Mn^{2+}$, 1 mM $Ca^{2+}$ plus 1 mM $Mg^{2+}$, 1 mM $Ca^{2+}$ plus 10 mM $Mg^{2+}$, 10 mM $Mg^{2+}$, or 10 mM $Mg^{2+}$ plus 10 µg/ml TS2/16 were treated with 5 nM $^3$H-known inhibitor alone or 5 nM $^3$H-known inhibitor plus 10 nM BIO1591 for 30 min at room temperature. The cells were then pelleted by centrifugation, resuspended in 100 µl of TBS plus $Mn^{2+}$, and analyzed by scintillation counting. Counts bound under these conditions measures integrin that is not occupied by the test compound and is therefore free to bind the $^3$H-known inhibitor.
Figure 5:
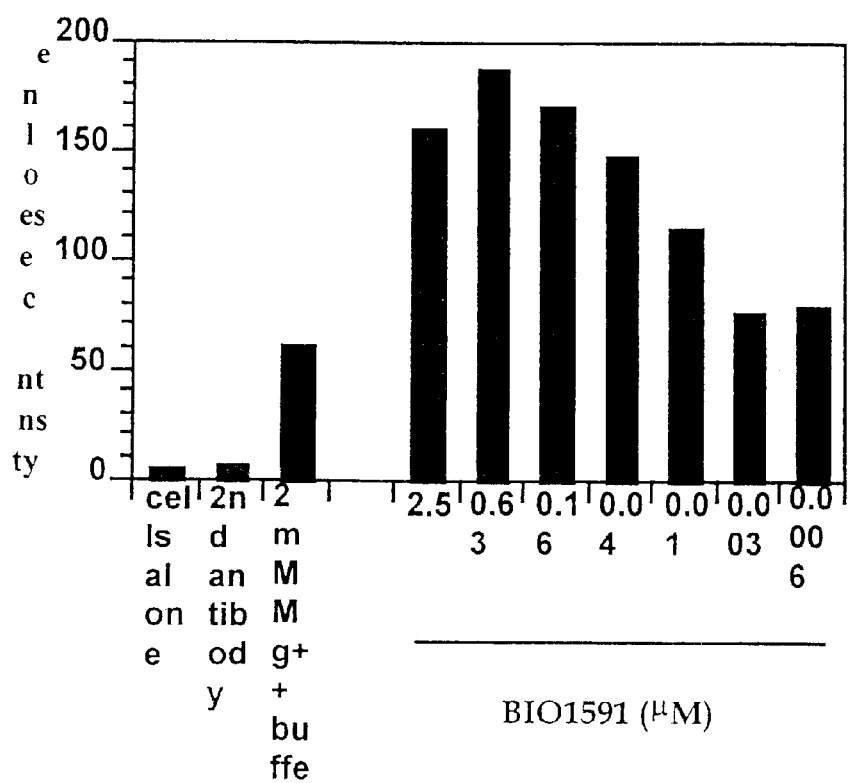

FIG. 5 shows that oMePUPA-V induced the exposure of the LIBS epitope as compared to 2 mM $Mg^{+2}$ buffer (Panel B). The induction was concentration dependent and similar in magnitude to the induction observed with 1 mM $Mn^{+2}$ (Panel A). Omission of the LIBS antibody and detecting antibody, or omission of the detecting antibody alone, eliminated labeling (Panel B). The $EC_{50}$ of the response was ~20 nM.

Conclusion

These data indicate that oMePUPA-V induces the same conformational change in VLA-4 as observed with native ligands. The LIBS values generally fall within the range defined by the binding and adhesion assays which are 8 nM and 22 nM, respectively, for oMePUPA-V.

6.2 The Multi-species Receptor Screen a. Receptor Affinity of oMePUPA-V as Measured in VCAM-Ig Direct Binding Assay Using VCAM-Ig Alkaline Phosphatase Conjugate and Peripheral Blood Lymphocytes or Spleen Cells From Various Species.

PBLs, were isolated from peripheral blood of humans, sheep and dogs using methods described for sheep PBL (Abraham, W. M. et al. J. Clin. Invest. 93:776–787, 1994). The VCAM-Ig-AP Competitive Binding Assay was used to compare the binding of oMePUPA-V to these different cell types.

The $IC_{50}$'s obtained for oMePUPA-V on peripheral blood lymphocytes or spleen cells from various species in the presence of $Mn^{+2}$ are shown in Table 6. In the presence of $Mn^{+2}$, oMePUPA-V inhibits with a similar $IC_{50}$ the binding VCAM-Ig to lymphocytes obtained from humans, rats, dogs, sheep, and mice. There is no evidence for species specificity. This is consistent with the high degree of sequence conservation observed among species for VLA-4 and its natural ligands, CS-1 and VCAM.

TABLE 6

Receptor affinity of oMePUPA-V as measured in VCAM-Ig Competitive Binding Assay using VCAM-IG Alkaline Phosphatase Conjugate and peripheral blood lymphocytes or spleen cells from various species

| Species | Source | Divalent Cation | $IC_{50}$ [nM] |
| --- | --- | --- | --- |
| Human | PBLs | $Mn^{+2}$ | 6 ± 1 (n = 3) |
| Sheep | PBLs | $Mn^{+2}$ | 3 ± 1 (n = 3) |
| Canine | PBLs | $Mn^{+2}$ | 13 ± 2 (n = 3) |
| Mouse | splenocytes | $Mn^{+2}$ | 4 ± 2 (n = 4) |
| rat | splenocytes | $Mn^{+2}$ | 5 ± 1 (n = 3) |

Example 7

Receptor Kinetics of oMePUPA-V 7.1 Competition Assay Using a $^3$H-known Inhibitor as a Probe Jurkat cells were maintained in RPMI-1640 medium plus 10% fetal bovine serum at 37° C. in a tissue culture incubator. For binding studies, the cells were pelleted by centrifugation, washed two times with TBS (50 mM Tris HCl, 150 mM NaCl, 0.1% bovine serum albumin, 2 mM glucose, 10 mM HEPES pH 7.4), suspended at approximately $2\times10^6$ cells/ml in TBS, and counted using a Neubauer hemocytometer. The cells were further diluted to $1.5\times10^6$/ml in the buffers indicated and subjected to the specific treatments defined for each experiment. The cells were then pelleted by centrifugation, resuspended in 100 μl of assay buffer, and transferred to a scintillation vial containing 2.9 ml of ScintiVerse II (Fisher Scientific). Cell-associated radioactivity was quantified by scintillation counting. Counts bound under these conditions measures integrin that is not occupied by the test compound and is therefore free to bind the $^3$H-known inhibitor. All studies were performed in siliconized 1.5 ml eppendorf tubes with a standard 1 ml sample volume. Non-specific binding of the $^3$H-known inhibitor to cells (background) was defined by measuring the inhibitor bound in the absence of metal ion. Specific counts bound were calculated by subtracting non-specific counts from total counts bound.

A series of competition studies were performed to verify that oMePUPA-V and the known inhibitor compete for the same site on VLA-4. First, the $^3$H-known inhibitor was mixed with an equimolar amount of oMePUPA-V, a 10-fold excess, and a 100-fold excess, incubated with Jurkat cells and the ability of the cold inhibitor to compete for binding of the known inhibitor assessed. oMePUPA-V treatment produced a dose-dependent inhibition of $^3$H-known inhibitor binding. The concentration of oMePUPA-V that was needed to compete $^3$H-known inhibitor binding was 10-fold greater than was needed when cold was used as a competitor, consistent with its lower affinity for $Mn^{+2}$-activated VLA-4. Second, $Mn^{+2}$-activated Jurkat cells were treated with $^3$H-known inhibitor in order to first occupy VLA-4 with the radioactive probe and then excess cold oMePUPA-V was added. Subsequent treatments with excess cold oMePUPA-V or known inhibitor were indistinguishable in their ability to displace the radioactive probe. Third, $Mn^{+2}$-activated Jurkat cells were treated with saturating amounts of oMePUPA-V, and the rate at which the oMePUPA-V dissociated was measured. Unlike the prolonged half life of the known inhibitor for $Mn^{+2}$-activated VLA-4, oMePUPA-V is rapidly released from the oMePUPA-V-VLA-4 with a $t_{1/2}$ of less than 10 min. The large difference in $t_{1/2}$ for oMePUPA-V and the known inhibitor suggests that the lower affinity of oMePUPA-V for VLA-4 is a result of its faster off rate.

Dissociation data reveals that binding of oMePUPA-V to VLA-4 is highly dependent on the activation state of VLA-4 and that it exhibits the same selectivity for activation seen with the known inhibitor. As with $Mn^{+2}$-activated VLA-4, the $t_{1/2}$ of oMePUPA-V dissociation from $Mg^{+2}$-activated VLA-4 was less than 10 min the shortest time point that can be assessed in the competition format. On the other hand, in the presence of $Mg^{+2}$ plus the activating antibody, TS2/16, the $t_{1/2}$ was prolonged (20 min). All of the possible activation states have not been assessed in detail, however a simple screen was devised that can rapidly highlight differences. In this assay, a fixed concentration of oMePUPA-V (10 nM) was mixed with 5 nM $^3$H-known inhibitor and binding was performed under these conditions at various states of activation. If oMePUPA-V had an abnormally high or low affinity for VLA-4 one would detect this by the difference in the amount of $^3$H-known inhibitor. The differences in percentage of $^3$H-known inhibitor bound under different activation conditions approximate what would be predicted based on the known properties of the inhibitor.

The binding studies verify that oMePUPA-V competes with the known inhibitor for binding to VLA-4 at concentrations consistent with its affinity and demonstrate that the two compounds compete for the same site on the integrin. The similarity of oMePUPA-V and the known inhibitor binding under various states of VLA-4 activation, suggest that the mechanism of binding is similar.

7.2 Assay of oMePUPA-V in Panlabs and Cerep Screens oMePUPA-V was tested in the Panlabs ProfilingScreen, DiscoveryScreen, and Immunoscreen panel of radioligand, enzyme, and functional assays and in the Cerep membrane receptor panel. No significant activity was observed for oMePUPA-V at 10 μM in any assay including the NK1 receptor assay, against which known inhibitors showed some activity.

Cerep also reported oMePUPA-V showed no inhibition against human ACE protease activity. The source of ACE proteases was human endothelial cells (HUVEC). $^3$H-HGG, added to HUVEC, was converted to $^3$H-hippuric acid and glycylglycine by ACE. Captopril, a potent ACE inhibitor, blocked the conversion with an $IC_{50}$ of 990 pM, while, oMePUPA-V at 10 μM, did not.

Pharmaceutical Properties:

oMePUPA-V is a white to off-white crystalline powder. It is soluble in DMSO and has an aqueous solubility of 0.120 mg/mL. The thermal behavior of oMePUPA-V studied by DSC, TGA and hot stage microscopy indicates that the material melts at approximately 160° C. At approximately 136° C. the DSC and TGA analyses suggest that oMePUPA-V loses a volatile impurity which maybe consistent with the dehydration of a monohydrate.

Formulation

Nebulization Formulation

The manufacturing directions for 100 mL of a 5 mg/mL oMePUPA-V nebulizationformulation are listed below.

Prepare 200 mL stock buffer solution as follows:
1. Weigh 0.286 g of Tromethamine, USP into a suitable container.
2. Weigh 1.676 g of Sodium Chloride, USP into the same container.
3. Add 200 mL of Water for Injection, USP.

Mix until homogenous.
1. Weigh 0.500 g of oMePUPA-V into a suitable container.
2. Add 100 mL of buffer prepared in step 1.
3. Mix until homogeneous.
4. Sterile filter into a suitable container.
5. Seal with a suitable closure.

Typical formulation properties:
pH: 7.4, Osmolality: 290 mOsm

EXAMPLE 9

Stability Indication HPLC Procedure

| | | |
|---|---|---|
| Column: | Zorbax ® SB-C18, 3 μm particle, 4.6 × 150 mm | |
| Guard Column: | Zorbax ® SB-C18, 5 μm particle, 4.6 × 12.5 mm | |
| Flow Rate: | 1 mL/min | |
| Column Temperature: | 40° C. | |
| Autosampler Temperature: | 4° C. | |
| Mobile Phase | A: 0.1% (w/v) trifluoroacetic acid (TFA) in water<br>B: 0.1% (w/v) TFA in 90% (v/v) acetonitrile, 10% (v/v) water | |
| Gradient: | | |
| | Time (min) | % B |
| | 0–3 | 15 |
| | 3–18 | 15 to 100 |
| | 18–21 | 100 |
| | 21–28 | 15 |
| Injection: | 10 μL of 0.2 mg/mL solutions in Tris/NaCl/water (bulk intermediate) or in 0.1% TFA/45% acetonitrile (final product). | |
| Detection: | UV 254 nm (primary) and 215 nm | |
| Control: | oMePUPA-V, heated in boiling water for 20 min. | |

The preliminary method qualification was completed.

Drug Substance Stability

No degradation was observed in the bulk intermediate stored for two weeks under the following storage conditions: at 40° C. in a closed vial; at 50° C. in a closed vial; at 25° C., RH 60%; and at 40° C., RH 75%. At four weeks, one or two degradation peaks became detectable at 40° C. and 50° C., but the level of each impurity peak was still less than 0.02%.

Solution Stability a) Nebulization formulation, 5 mg/mL in Tris/NaCl, stored at room temperature for two months showed early eluting degradation peaks at a total level of 1% (at 254 nm) and 2–3% (at 215 nm).

b) Heating nebulization formulation in boiling water for 20 min decreased the purity from 99.9% to 98.7% at 254 nm and from 100% to 93.6% at 215 nm.
c) The 0.2 mg/mL solution in Tris/NaCl/water at neutral pH is stable at 2–8° C. at least for a week.

It will be apparent to those skilled in the art that various modifications and variations can be made in the claimed invention without departing from the spirit or scope of the invention. Thus it is intended that the present invention cover the modifications and variations of this invention provided that they come within the scope of the appended claims and their equivalents.

What is claimed is:

1. A cell adhesion inhibitory compound

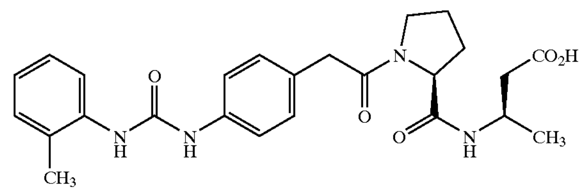

BIO 1591 or a pharmaceutically acceptable derivative, prodrug, or salt thereof.

2. A pharmaceutical composition comprising a compound according to claim 1 and a pharmaceutically acceptable carrier.

3. A pharmaceutical composition comprising the adhesion inhibitory compound

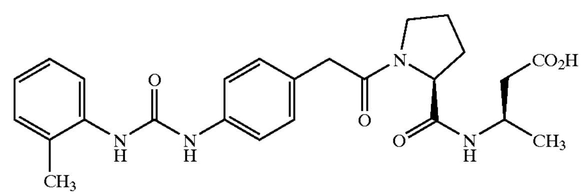

BIO 1591 or a salt thereof, and a pharmaceutically acceptable carrier.

4. The pharmaceutical composition according to claim 2 additionally comprising a second agent selected from the group consisting of corticosteriods, bronchodilators, antiasthmatics, antiinflammatories, antirheumatics, immunosuppressants, antimetabolites, immunomodulators, antipsoriatics and antidiabetics.

5. A pharmaceutical composition comprising the inhibitory compound of claim 1 and one or more cell adhesion inhibitor compounds.

6. The pharmaceutical composition of claim 5, wherein said one or more cell adhesion inhibitor compounds is a VLA-4 inhibitor.

7. A method for preventing, inhibiting or suppressing cell adhesion in a mammal comprising the step of administering to said mammal an effective amount of the pharmaceutical composition of claim 2 or claim 3.

8. The method of claim 7 wherein said method is used for preventing, inhibiting, or suppressing inflammation.

9. A method for treating asthma, allergic rhinitis, multiple sclerosis, atherosclerosis, inflammatory bowel disease or multiple myeloma in a mammal comprising administering to said mammal a therapeutically effective amount of a compound of claim 1 or a pharmaceutical composition of claim 3.

10. A method for treating multiple sclerosis in a mammal comprising administering to said mammal a therapeutically effective amount of a compound of claim 1 or a pharmaceutical compostion of claim 3.

11. A method for treating inflammatory bowel disorders in a mammal comprising administering to said mammal a therapeutically effective amount of a compound of claim 1 or a pharmaceutical composition of claim 3.

12. A pharmaceutical composition comprising an ester prodrug of the compound of claim 1.

13. A method for treating preventing or ameliorating the symptoms of asthma comprising administration to a patient suffering from asthma a therapeutically effective amount of a compound of claim 1 or a pharmaceutical compostition of claim 3.

14. The compound according to claim 1, wherein the prodrug is an ester prodrug.

15. The compound according to claim 14, wherein the ester prodrug is prepared by reacting the compound BIO 1591 with a straight or branched $C_{1-10}$ alcohol.

16. The compound according to claim 14, wherein the ester prodrug is prepared by reacting the compound BIO 1591 with a straight or branched $C_{1-4}$ alcohol.

17. The compound according to claim 14, wherein the ester prodrug is of the following formula:

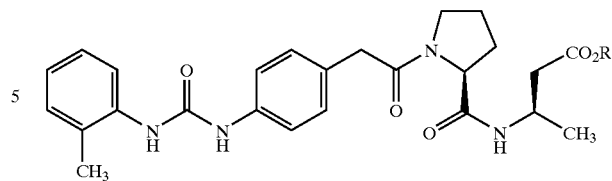

wherein R is a straight or branched $C_{1-10}$ alkyl.

18. The compound according to claim 17, wherein R is a straight or branched $C_{1-4}$ alkyl.

19. A cell adhesion inhibitory compound of the following formula

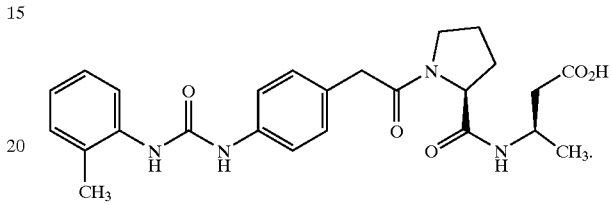

BIO 1591

* * * * *